US009814759B2

(12) United States Patent
Wong et al.

(10) Patent No.: US 9,814,759 B2
(45) Date of Patent: Nov. 14, 2017

(54) PHARMACEUTICAL COMPOSITION COMPRISING RECOMBINANT HEMOGLOBIN PROTEIN OR SUBUNIT-BASED THERAPEUTIC AGENT FOR CANCER TARGETING TREATMENT

(71) Applicant: Cheer Global Ltd., Hong Kong (HK)

(72) Inventors: Bing Lou Wong, Irvine, CA (US); Norman Fung Man Wai, Vancouver (CA); Sui Yi Kwok, Hong Kong (HK)

(73) Assignee: Cheer Global Ltd., Hong Kong (HK)

( * ) Notice: Subject to any disclaimer, the term of this patent is extended or adjusted under 35 U.S.C. 154(b) by 0 days.

(21) Appl. No.: 14/752,999

(22) Filed: Jun. 28, 2015

(65) Prior Publication Data

US 2016/0000864 A1    Jan. 7, 2016

(51) Int. Cl.
  *A61K 38/42*    (2006.01)
  *C07K 14/805*   (2006.01)
  *A61K 38/17*    (2006.01)
  *A61K 45/06*    (2006.01)
  *A61K 47/48*    (2006.01)
  *A61K 31/7068*  (2006.01)

(52) U.S. Cl.
  CPC ...... *A61K 38/1709* (2013.01); *A61K 31/7068* (2013.01); *A61K 38/42* (2013.01); *A61K 45/06* (2013.01); *A61K 47/48307* (2013.01); *C07K 14/805* (2013.01)

(58) Field of Classification Search
  CPC . A61K 47/48307; A61K 38/42; C07K 14/805
  See application file for complete search history.

(56) References Cited

U.S. PATENT DOCUMENTS

| 4,600,531 | A | | 7/1986 | Walder |
| 5,661,124 | A | | 8/1997 | Hoffman et al. |
| 5,679,777 | A | * | 10/1997 | Anderson ............... C12N 15/81 424/193.1 |
| 5,739,011 | A | | 4/1998 | Anderson et al. |
| 5,798,227 | A | * | 8/1998 | Hoffman .......... A61K 47/48307 435/252.33 |
| 5,827,693 | A | * | 10/1998 | De Angelo ............ C12N 15/81 435/254.2 |
| 7,932,356 | B1 | | 4/2011 | Wong et al. |
| 7,989,593 | B1 | | 8/2011 | Wong et al. |
| 8,048,856 | B1 | | 11/2011 | Wong et al. |
| 8,084,581 | B1 | | 12/2011 | Wong et al. |
| 8,106,011 | B1 | | 1/2012 | Wong et al. |
| 8,742,073 | B2 | | 6/2014 | Wong et al. |
| 9,056,098 | B2 | | 6/2015 | Wong et al. |
| 2006/0276374 | A1 | * | 12/2006 | Dewhirst ............... A61K 31/21 514/13.5 |
| 2009/0023632 | A1 | * | 1/2009 | Adamson ......... A61K 47/48307 514/1.1 |
| 2014/0106004 | A1 | * | 4/2014 | Wong .................... A61K 33/38 424/649 |
| 2014/0335018 | A1 | * | 11/2014 | Wong .................... A61K 45/06 424/1.69 |

FOREIGN PATENT DOCUMENTS

WO    2014059199 A1    4/2014

OTHER PUBLICATIONS

Trent et al. "A Ubiquitously Expressed Human Hexacoordinate Hemoglobin" The Journal of Biological Chemistry vol. 277, No. 22, Issue of May 31, pp. 19538-19545, 2002.*
Guidance for Industry and Reviewers—Estimating the Safe Starting Dose in Clinical Trials for Therapeutics in Adult Healthy Volunteers, U.S. Department of Health and Human Services, Food and Drug Administration, Center for Drug Evaluation and Research (CDER), Center for Biologics Evaluation and Research (CBER), Dec. 2002, Pharmacology and Toxicology.
International Search Report and Written Opinion for corresponding PCT application PCT/CN2015/083041.

* cited by examiner

*Primary Examiner* — Christina Bradley
(74) *Attorney, Agent, or Firm* — Spruson & Ferguson (HK)

(57) ABSTRACT

The present invention provides a pharmaceutical composition containing recombinant hemoglobin protein or tetramer or dimer or subunit for tissue oxygenation and treating cancer. The recombinant hemoglobin protein or tetramer or dimer or subunit-based therapeutic agent is also effective for treating cancer. The recombinant hemoglobin or tetramer or dimer or its subunit moiety can target cancer cells and the therapeutic moiety (i.e. active agent/therapeutic drug) can kill the cancer cells efficiently. The recombinant hemoglobin or tetramer or dimer or its subunit-based therapeutic agent used in the present invention can be used in the treatment of various cancers such as pancreatic cancer, leukemia, head and neck cancer, colorectal cancer, lung cancer, breast cancer, liver cancer, nasopharyngeal cancer, esophageal cancer, prostate cancer, stomach cancer and brain cancer. The composition can be used alone or in combination with other therapeutic agent(s) such as chemotherapeutic agent, radiotherapeutic agent, anti-cancer protein drug to give a synergistic effect on cancer treatment, inhibiting metastasis and/or reducing recurrence.

25 Claims, 18 Drawing Sheets

(A) Recombinant Hemoglobin Subunit/Monomer (1) Homo sapiens hemoglobin monomer, alpha (α) subunit, 141 aa. (SEQ. ID No. 1)

|— 141aa —|

(2) Homo sapiens hemoglobin monomer, beta (β) subunit, 146 aa. (SEQ. ID No. 2)

|— 146aa —|

(3) Homo sapiens hemoglobin monomer, gamma 1 (γ1) subunit, 146aa. (SEQ. ID No. 3)

|— 146aa —|

(4) Homo sapiens hemoglobin monomer, gamma 2 (γ2) subunit, 146aa. (SEQ ID No. 4)

|— 146aa —|

(B) Recombinant Hemoglobin Dimer (5) Recombinant hemoglobin dimer, αβ

(6) Recombinant hemoglobin dimer, αγ1

(7) Recombinant hemoglobin dimer, αγ2

(8) Recombinant hemoglobin dimer, βγ1

(9) Recombinant hemoglobin dimer, βγ2

(C) Recombinant Hemoglobin Tetramer

(10) Recombinant Hemoglobin Tetramer, 2αβ$_2$

(11) Recombinant Hemoglobin Tetramer, 2αγ1$_2$

(12) Recombinant Hemoglobin Tetramer, 2αγ2$_2$

(13) Recombinant Hemoglobin Tetramer, 2βγ1$_2$

| Final culture volume | 1350ml |
|---|---|
| Mass of cell pellet (wet weight) | 77.6g |
| Final protein yield | 0.18g/L |

(A)

(B)

(A)

p50 of recombinant hemoglobin tetramer ($2\alpha\beta_2$): 15 mmHg (B)

p50 of recombinant hemoglobin tetramer ($2\alpha\gamma1_2$): 21 mmHg (A)

(Model compound)

(B)

SEQUENCE LISTING

```
<160> NUMBER OF SEQ ID NOS: 4

<210> SEQ ID NO 1
<211> LENGTH: 141
<212> TYPE: PRT
<213> ORGANISM: Homo sapiens

<400> SEQUENCE: 1

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
```

```
                85                  90                  95
Asn Phe Lys Leu Leu Ser His Cys Leu Leu Val Thr Leu Ala Ala His
            100                 105                 110
Leu Pro Ala Glu Phe Thr Pro Ala Val His Ala Ser Leu Asp Lys Phe
            115                 120                 125
Leu Ala Ser Val Ser Thr Val Leu Thr Ser Lys Tyr Arg
            130                 135                 140

<210> SEQ ID NO 2
<211> LENGTH: 146
<212> TYPE: PRT
<213> ORGANISM: Homo sapiens

<400> SEQUENCE: 2

Val His Leu Thr Pro Glu Glu Lys Ser Ala Val Thr Ala Leu Trp Gly
1               5                   10                  15
Lys Val Asn Val Asp Glu Val Gly Gly Glu Ala Leu Gly Arg Leu Leu
            20                  25                  30
Val Val Tyr Pro Trp Thr Gln Arg Phe Phe Glu Ser Phe Gly Asp Leu
            35                  40                  45
Ser Thr Pro Asp Ala Val Met Gly Asn Pro Lys Val Lys Ala His Gly
        50                  55                  60
Lys Lys Val Leu Gly Ala Phe Ser Asp Gly Leu Ala His Leu Asp Asn
65                  70                  75                  80
Leu Lys Gly Thr Phe Ala Thr Leu Ser Glu Leu His Cys Asp Lys Leu
                85                  90                  95
His Val Asp Pro Glu Asn Phe Arg Leu Leu Gly Asn Val Leu Val Cys
            100                 105                 110
Val Leu Ala His His Phe Gly Lys Glu Phe Thr Pro Pro Val Gln Ala
            115                 120                 125
Ala Tyr Gln Lys Val Val Ala Gly Val Ala Asn Ala Leu Ala His Lys
            130                 135                 140
Tyr His
145

<210> SEQ ID NO 3
<211> LENGTH: 146
<212> TYPE: PRT
<213> ORGANISM: Homo sapiens

<400> SEQUENCE: 3

Gly His Phe Thr Glu Glu Asp Lys Ala Thr Ile Thr Ser Leu Trp Gly
1               5                   10                  15
Lys Val Asn Val Glu Asp Ala Gly Gly Glu Thr Leu Gly Arg Leu Leu
            20                  25                  30
Val Val Tyr Pro Trp Thr Gln Arg Phe Phe Asp Ser Phe Gly Asn Leu
            35                  40                  45
Ser Ser Ala Ser Ala Ile Met Gly Asn Pro Lys Val Lys Ala His Gly
        50                  55                  60
Lys Lys Val Leu Thr Ser Leu Gly Asp Ala Thr Lys His Leu Asp Asp
65                  70                  75                  80
Leu Lys Gly Thr Phe Ala Gln Leu Ser Glu Leu His Cys Asp Lys Leu
                85                  90                  95
His Val Asp Pro Glu Asn Phe Lys Leu Leu Gly Asn Val Leu Val Thr
            100                 105                 110
Val Leu Ala Ile His Phe Gly Lys Glu Phe Thr Pro Glu Val Gln Ala
```

-continued

```
                115               120                 125
Ser Trp Gln Lys Met Val Thr Ala Val Ala Ser Ala Leu Ser Ser Arg
        130               135               140

Tyr His
145

<210> SEQ ID NO 4
<211> LENGTH: 146
<212> TYPE: PRT
<213> ORGANISM: Homo sapiens

<400> SEQUENCE: 4

Gly His Phe Thr Glu Glu Asp Lys Ala Thr Ile Thr Ser Leu Trp Gly
1               5                   10                  15

Lys Val Asn Val Glu Asp Ala Gly Gly Glu Thr Leu Gly Arg Leu Leu
            20                  25                  30

Val Val Tyr Pro Trp Thr Gln Arg Phe Phe Asp Ser Phe Gly Asn Leu
        35                  40                  45

Ser Ser Ala Ser Ala Ile Met Gly Asn Pro Lys Val Lys Ala His Gly
    50                  55                  60

Lys Lys Val Leu Thr Ser Leu Gly Asp Ala Ile Lys His Leu Asp Asp
65                  70                  75                  80

Leu Lys Gly Thr Phe Ala Gln Leu Ser Glu Leu His Cys Asp Lys Leu
                85                  90                  95

His Val Asp Pro Glu Asn Phe Lys Leu Leu Gly Asn Val Leu Val Thr
            100                 105                 110

Val Leu Ala Ile His Phe Gly Lys Glu Phe Thr Pro Glu Val Gln Ala
        115                 120                 125

Ser Trp Gln Lys Met Val Thr Gly Val Ala Ser Ala Leu Ser Ser Arg
    130                 135                 140

Tyr His
145
```

PHARMACEUTICAL COMPOSITION COMPRISING RECOMBINANT HEMOGLOBIN PROTEIN OR SUBUNIT-BASED THERAPEUTIC AGENT FOR CANCER TARGETING TREATMENT

CROSS-REFERENCE TO RELATED APPLICATIONS

The present application claims priority from the U.S. provisional patent application Ser. No. 62/019,925 filed Jul. 2, 2014, and the disclosure of which is incorporated herein by reference in its entirety.

COPYRIGHT NOTICE/PERMISSION

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. The following notice applies to the processes, experiments, and data as described below and in the drawings attached hereto: Copyright © 2014-15, All Rights Reserved.

TECHNICAL FIELD

The present invention provides recombinant hemoglobin protein, recombinant hemoglobin tetramer, dimer and subunit including α, β, γ1, γ2 monomer (with or without heme molecule) with oxygen carrying capacity to replace the natural hemoglobin protein. The invention also provides method of using the recombinant hemoglobin protein, the recombinant hemoglobin tetramer, dimer or subunit for use in oxygenation of in vivo and ex vivo tissue. The present invention further provides recombinant hemoglobin protein-, the recombinant hemoglobin tetramer-, dimer-, or subunit-based therapeutic agent that at least one of the hemoglobin subunit has been chemically modified to create a material having the ability to target and/or kill cancer cells. The present invention additionally provides a method for construction and expression of different recombinant hemoglobin subunits including α, β, γ1, γ2 monomer (with or without heme molecule), and the dimer and tetramer thereof and for chemical modification or engineering thereof. The present invention further describes a design for chemical engineering for creating a recombinant hemoglobin protein or recombinant hemoglobin tetramer, dimer or subunit-based therapeutic agent. The present invention further relates to recombinant hemoglobin protein or recombinant hemoglobin tetramer, dimer or subunit-based therapeutic agent-containing pharmaceutical compositions for cancer targeting treatment in humans and other animals, in particular, for liver cancer, breast cancer, pancreatic cancer, and tumor induced or associated with respective progenitor cells.

BACKGROUND OF INVENTION

Hemoglobin-based oxygen carriers (HBOCs) were initially developed as blood substitutes. Human placenta hemoglobin is a particularly promising HBOC. It allows transporting more oxygen to hypoxic tissues owing to its higher oxygen affinity, lower viscosity, and smaller mean diameter than human red blood cells. However, the major problems posed by the use of placenta hemoglobin on a large scale are caused by the conditions under which it is extracted from the placentas and purified. Placentas are kept in frozen storage and to extract hemoglobin they have to be crushed before thawing. Then, tissues and fibrinogen are removed by filtration and several steps of chromatography, precipitation and diafiltration are carried out on the resulting filtrate. Also, the sources of human placenta hemoglobin and human blood are limited. Therefore, the construction and expression of recombinant hemoglobin protein or recombinant hemoglobin tetramer or dimer or subunits are important to solve this issue.

Hypoxia is common in cancers. Hypoxia and anemia (which contributes to tumor hypoxia) can lead to ionizing radiation and chemotherapy resistance by depriving tumor cells of the oxygen essential for the cytotoxic activities of these agents. Hypoxia may also reduce tumor sensitivity to radiation therapy and chemotherapy through one or more indirect mechanisms that include proteomic and genomic changes. Therefore, there is a need for improved cancer-treatment compositions, particularly, improved cancer-treatment compositions that facilitate targeting cancer cells and enhance the efficacy of cytotoxic agents.

SUMMARY OF THE INVENTION

Accordingly, in the present invention, a recombinant hemoglobin protein, recombinant hemoglobin tetramer, dimer, and/or subunit is/are constructed with oxygen carrying capacity. The present invention provides recombinant hemoglobin protein, recombinant hemoglobin tetramer, dimer and subunit including α, β, γ1, γ2 monomer (with or without heme molecule) with oxygen carrying capacity to replace the natural hemoglobin protein. In addition, a therapeutic agent based on any of the recombinant hemoglobin protein, recombinant hemoglobin tetramer, dimer, and/or subunit of the present invention capable of targeting cancer cells in order to efficiently kill cancer cells by a conjugated therapeutic drug (e.g. chemotherapeutic agent, radiotherapeutic agent, anti-cancer protein drug) is provided. Common chemotherapeutic agents, radiotherapeutic agents and anti-cancer protein drugs which are widely used in different patients, however, have many side-effects are found. These problems can be overcome by chemically modifying any of the recombinant hemoglobin protein, tetramer, dimer, or subunit(s) of the present invention and linking thereof to one or more therapeutic drugs. Therefore, the present invention further provides recombinant hemoglobin protein-, the recombinant hemoglobin tetramer-, dimer-, or subunit-based therapeutic agent that has been chemically modified to create a material having the ability to target and/or kill cancer cells. The present invention additionally provides a method for construction and expression of different recombinant hemoglobin subunits including α, β, γ1, γ2 monomer (with or without heme molecule), and the dimer and tetramer thereof and for chemical modification or engineering thereof. The present invention further describes a design for chemical engineering for creating a recombinant hemoglobin protein or recombinant hemoglobin tetramer, dimer or subunit-based therapeutic agent. The present invention further relates to recombinant hemoglobin protein or recombinant hemoglobin tetramer, dimer or subunit-based therapeutic agent-containing pharmaceutical compositions for cancer targeting treatment in humans and other animals, in particular, for liver cancer, breast cancer, pancreatic cancer, and tumor induced or associated with respective progenitor cells. When compared to the conventional therapeutic drugs alone for treating cancer (e.g. chemotherapeutic drug including 5-Fluorouracil, Temozolomide, Cisplatin), the recombinant hemoglobin protein-, tetramer-, dimer- or subunit-based therapeutic agents of the present invention not only can target cancer cells, but are much more efficacious in the treatment of cancer and/or tumors since the killing effect on the cancer cells/tumor is further enhanced. Further, since the cancer-targeting recombinant hemoglobin protein or recombinant hemoglobin tetramer or dimer or subunit-based therapeutic agents can be used in a relatively lower dose than other known hemoglobin-based oxygen carriers, the adverse side effect from the conventional therapeutic drug for cancers is greatly attenuated.

Most conventional therapeutic drugs are very expensive. The treatment cost can be cut down significantly for each patient if the therapeutically effective dose is lowered. Recombinant hemoglobin protein or recombinant hemoglobin subunit-based therapeutic agents of the present invention are a good candidate for lowering the therapeutically effective dose as the modified recombinant hemoglobin protein or recombinant hemoglobin subunit can target cancer cells. In one embodiment, the therapeutically effective dose of the recombinant hemoglobin protein or recombinant hemoglobin tetramer or dimer or subunit-based therapeutic agent for treating cancer in human can be 0.0024 mg/kg (for a single dose) of the subject's body weight or lower. It can be used in treating cancer in multiple doses (once per week). The invention also provides method of using the recombinant hemoglobin protein, the recombinant hemoglobin tetramer, dimer or subunit for use in oxygenation of in vivo and ex vivo tissue.

Optionally, the presently claimed recombinant hemoglobin protein or recombinant hemoglobin tetramer or dimer or subunit-based therapeutic agent can also be linked to fluorescent probe(s) to facilitate the live-cell imaging. The recombinant hemoglobin protein or tetramer or dimer or subunit-based therapeutic agent conjugated with fluorescein can be taken up by liver cancer cells. The uptake of freshly fluorescein conjugated recombinant hemoglobin protein- or tetramer- or dimer- or subunit-based therapeutic agents by cells is verified by immediately employing the same to the cells in a series of live cell uptake studies as described hereinafter. In one example, the fluorescein conjugated recombinant hemoglobin protein- or tetramer- or dimer- or subunit-based therapeutic agent is shown to be taken up by liver cancer cells (e.g. HepG2 cell line).

Therefore, in the first aspect of the present invention, different recombinant hemoglobin proteins, recombinant tetramer, recombinant dimer, and/or recombinant hemoglobin subunits (e.g. α, β, γ1, γ2; with or without heme molecule), and the dimer and tetramer being formed thereof are provided, and said recombinant hemoglobin proteins, tetramer, dimer, and subunits are also provided for further chemical engineering or modification. A method for constructing and expressing said recombinant hemoglobin proteins or subunit(s), and the dimer and tetramer thereof in a host is also provided.

The second aspect of the present invention is to construct a chemically modified recombinant hemoglobin protein or recombinant hemoglobin tetramer, dimer or subunit with one or more functional groups that can be used as a linkage or linker (cleavable or non-cleavable) to at least one type of therapeutic drug for targeting the cancer cells. In one embodiment, the chemical reactions involved in chemically modifying the recombinant hemoglobin protein or recombinant hemoglobin tetramer, dimer or subunit of the present invention include but not limited to amine reactions, thiol reactions, carboxylate reactions, hydroxyl reactions, native chemical ligations using thioesters, incorporation of bioorthogonal functionalities, photochemical reactions, and metal-mediated reactions. One or more hemoglobin subunits of the recombinant hemoglobin protein can be chemically modified.

The third aspect of the present invention is to chemically link the recombinant hemoglobin protein or recombinant hemoglobin tetramer, dimer or subunit of the present invention to at least one type of therapeutic drug (active agent) via said cleavable or non-cleavable linkage or linker in order to kill the cancer cells. The therapeutic drug or active agent which can be linked to the recombinant hemoglobin protein or recombinant hemoglobin tetramer, dimer or subunit of the present invention includes but is not limited to a chemotherapeutic drug (e.g., 5-Fluorouracil, Temozolomide, Cisplatin), a radiotherapeutic drug (e.g., Rhodium-105 complex, Samarium-153 complex and other related complex), an anti-cancer protein drug (e.g. arginase, arginine deiminase), any other therapeutic drug and/or compound which is proven to be effective for treating and/or alleviating cancer and capable of being readily linked to the recombinant hemoglobin protein or recombinant hemoglobin tetramer, dimer or subunit of the present invention, through the cleavable or non-cleavable linkage or linker to the recombinant hemoglobin protein or recombinant hemoglobin tetramer, dimer or subunit or to the chemically modified recombinant hemoglobin protein or recombinant hemoglobin tetramer, dimer or subunit in the second aspect of the present invention.

The present invention further relates to recombinant hemoglobin protein or recombinant hemoglobin tetramer, dimer or subunit-based therapeutic agent-containing pharmaceutical composition for cancer targeting treatment in humans and other animals. The composition includes a therapeutically effective amount of said therapeutic agent and a pharmaceutically acceptable carrier, salt, buffer, water, or a combination thereof, in order for targeting and treating cancer. In one embodiment, the pharmaceutical composition has a pH in a range of 5.5 to 9.5. In another embodiment, the pharmaceutical composition has a pH in a range of 7.2 to 8.0.

In the fourth aspect of the present invention, it is provided a method for targeting and/or treating cancer comprising administering a pharmaceutical composition comprising a therapeutically effective amount of the recombinant hemoglobin protein or recombinant hemoglobin tetramer, dimer or subunit-based therapeutic agent of the present invention to a subject in need thereof suffering from various tumors and/or cancers. The composition can be administered to the subject by various routes including but not limited to intravenous injection, intraperitoneal injection, and subcutaneous injections. Both cleavable and non-cleavable forms of the recombinant hemoglobin protein or recombinant hemoglobin tetramer, dimer or subunit-based therapeutic agent containing an active agent such as chemotherapeutic agent (e.g. 5-Fluorouracil, 5FU) can be prepared for cancer targeting treatment in the present invention.

The recombinant hemoglobin protein or recombinant hemoglobin tetramer, dimer or subunit-based therapeutic agent of the present invention is also chemically modified to facilitate the targeting of the therapeutic agent to cancer cells such that it is more efficient to kill the cancer cells. The recombinant hemoglobin protein or recombinant hemoglobin tetramer, dimer or subunit can be chemically modified and linked to different therapeutic agents (e.g. 5FU, Temozolomide, Cisplatin, etc). The recombinant hemoglobin protein or recombinant hemoglobin tetramer, dimer or subunit can target cancer cells. This targeting property facilitates killing cancerous cells, cancer stem cells and/or cancer progenitor cells efficiently via inducing apoptosis of these cells. As such, a dose of the therapeutic agent can be lowered.

The recombinant hemoglobin protein or recombinant hemoglobin tetramer, dimer or subunit-based therapeutic agent provided in the present invention can be used in the treatment of various cancers such as pancreatic cancer, leukemia, head and neck cancer, colorectal cancer, lung cancer, breast cancer, liver cancer, nasopharyngeal cancer, esophageal cancer and brain cancer. The present invention is directed to recombinant hemoglobin protein or recombinant hemoglobin tetramer, dimer or subunit-based therapeutic agent, to methods of treating cancer, and to methods of treating and/or inhibiting metastasis of cancerous tissue and recurrence of cancerous tissue, including but not limited to liver cancer.

Cells within a tumor are heterogeneous in nature. A tumor is generally thought to be made up of (1) a majority of cancer cells with limited ability to divide, and (2) a rare population of cancer stem-like cells (CSCs), also known as progenitor cells, which can form new tumor cells and are highly metastatic in nature. Due to their inherent properties of being chemoresistant and metastatic, CSCs have been postulated to be responsible for recurrence in cancer patients.

Since the recombinant hemoglobin protein or recombinant hemoglobin tetramer, dimer or subunit moiety of the present recombinant hemoglobin protein or tetramer, dimer or subunit-based therapeutic agent can bring oxygen to CSCs or progenitor cells to facilitate killing of the cancer stem cells or the progenitor cells while the active agent moiety of the present recombinant hemoglobin protein or subunit-based therapeutic agent can kill the cancer cells, the present recombinant hemoglobin protein or recombinant hemoglobin tetramer, dimer or subunit-based therapeutic agent of the present invention has a synergistic effect in cancer treatment.

DEFINITIONS

Figure 1:
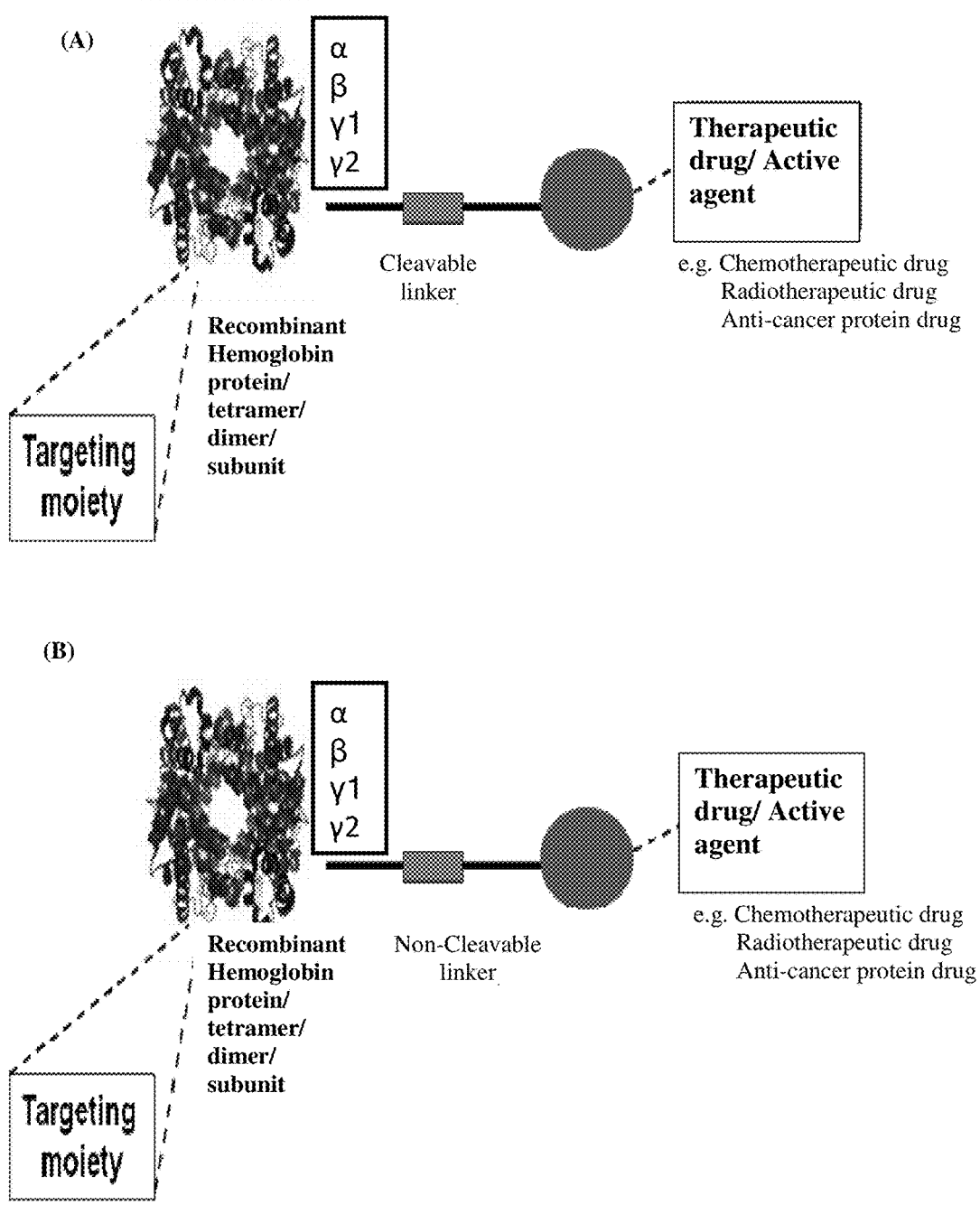
FIG. 1 shows the design approach for construction of recombinant hemoglobin protein or recombinant hemoglobin tetramer, dimer or subunit-based therapeutic agent. One or more therapeutic drugs can be linked to recombinant hemoglobin protein or recombinant hemoglobin tetramer, dimer or subunit (e.g. $\alpha$, $\beta$, $\gamma1$, $\gamma2$) to form the recombinant hemoglobin protein or recombinant hemoglobin tetramer, dimer or subunit-based therapeutic agent. The recombinant hemoglobin protein or recombinant hemoglobin tetramer, dimer or subunit can be chemically linked to therapeutic agent via cleavable (A) or non-cleavable linker/linkage (B). Cleavable linkers can be but not limited to carbinolamine, disulfide, carbamide, aminal, carbonate, ester, carbamate, phosphate, amide, acetal, imine, ether, and sulfonamide groups; non-cleavable linkers can be but not limited to alkyl and aryl groups.

The term "cancer stem cell" refers to a biologically distinct cell within a neoplastic clone that is capable of initiating and sustaining tumor growth in vivo (i.e. the cancer-initiating cell).

The term "cleavable conjugate" refers to a conjugate with at least one cleavable linker or linkage that can easily release a linked therapeutic drug/active agent by hydrolysis or redox reaction.

The term "non-cleavable conjugate" refers to a conjugate with at least one non-cleavable linker or linkage and it cannot easily release a linked therapeutic drug/active agent by hydrolysis or redox reaction.

The term "recombinant hemoglobin protein/proteins" refers to hemoglobin molecule in a molecular size of at least approximately 65 KDa and synthesized by any standard molecular chemistry techniques and not being isolated or purified from any animal or human source. In the present invention, the recombinant hemoglobin protein/proteins can include but not limited to the recombinant hemoglobin tetramer, dimer, and subunit (monomer) of the present invention (with or without heme) or be used interchangeably with the recombinant hemoglobin tetramer.

The term "recombinant hemoglobin tetramer" refers to hemoglobin molecule in a molecular size of at least approximately 64 KDa and synthesized by any standard molecular chemistry technique and not being isolated or purified from any animal or human source. In the present invention, the recombinant hemoglobin tetramer can comprise any four of the recombinant hemoglobin subunits described herein (with or without heme) or any four of the hemoglobin subunits synthesized by any standard molecular chemistry technique and not being isolated or purified from any animal or human source.

The term "recombinant hemoglobin dimer" refers to hemoglobin molecule in a molecular size of at least approximately 32 KDa and synthesized by any standard molecular chemistry techniques and not being isolated or purified from any animal or human source. In the present invention, the recombinant hemoglobin dimer can comprise any two of the recombinant hemoglobin subunits described herein or any two of the hemoglobin subunits synthesized by any standard molecular chemistry technique and not being isolated or purified from any animal or human source.

The term "recombinant hemoglobin subunit/subunits" refers to hemoglobin subunit or a fragment thereof in a molecular size of approximately 16 KDa or less and synthesized by standard molecular chemistry techniques and not being isolated or purified from animal or human source, which can be modified with or without heme group.

DETAILED DESCRIPTION OF THE INVENTION

Since most cancerous tissues, such as cancerous tumors, are hypoxic, they can become resistant to conventional chemotherapeutic/radiotherapeutic agent. Recombinant hemoglobin proteins or recombinant hemoglobin tetramer or dimer or subunits of the present invention can be used to alleviate this hypoxic condition. It allows transporting more oxygen to hypoxic tissues owing to its higher oxygen affinity, lower viscosity, and smaller mean diameter than human red blood cells, leading to reduction of chemotherapeutic/radiotherpeutic/other anti-cancer drug-resistance in cancer cells.

In one embodiment of the present invention, the recombinant hemoglobin protein or tetramer or dimer or subunit is produced. The recombinant hemoglobin protein or tetramer or dimer or subunit has the oxygen transport feature and can target cancerous cells or tissues in a human or animal body. The recombinant hemoglobin protein or recombinant hemoglobin tetramer or dimer or subunit of the present invention as an oxygen carrier is chemically modified and linked to at least one type of therapeutic drug, e.g., the chemotherapeutic agent, capable for triggering a receptor-mediated mechanism and leading a combined/conjugated chemotherapeutic agent to localize together with the recombinant hemoglobin protein or recombinant hemoglobin tetramer or dimer or subunit in at least the cytoplasm of the cancerous cells in order to increase the efficacy of both recombinant hemoglobin protein or tetramer or dimer or subunit and the chemotherapeutic agent in reducing tumor size leading to treatment of cancer. Preferably, said cancer is resistant to conventional therapeutic drugs such as chemotherapeutic and/or radiotherapeutic agents when administered solely.

A design for construction of a recombinant hemoglobin protein or recombinant hemoglobin tetramer or dimer or subunit-based therapeutic drug is shown in FIG. 1A and FIG. 1B. One or more active agents (or "therapeutic drug" are used interchangeably herein) are linked to the recombinant hemoglobin protein or recombinant hemoglobin tetramer or dimer or subunit to form the presently claimed recombinant hemoglobin protein- or subunit-based therapeutic agent. The selection of one or more particular active agent(s) can be made depending upon the type of cancer tissue to be targeted and the desired molecular size of the resulting chemically modified material. Furthermore, the selected active agents may be the same or different in the case of more than one active agents. That is, an active agent (or "therapeutic drug"), etc., as long as the resultant molecule retains the efficacy and is also able to link with the recombinant hemoglobin protein or tetramer or dimer or subunit of the present invention for targeting the cancer cells. The recombinant hemoglobin protein or tetramer or dimer or subunit of the present invention can be chemically linked to therapeutic drug/active agent via cleavable (FIG. 1A) or non-cleavable linkage or link (FIG. 1B) or, alternatively, can be directly conjugated with the active agent in the absence of said linkage or link. Different chemical groups can be used for chemical modification of the recombinant hemoglobin protein or tetramer or dimer or subunit in the present invention and the recombinant hemoglobin protein or tetramer or dimer or subunit can be linked to the therapeutic drug/active agent via these chemical groups. In one embodiment, the cleavable linkers can be but are not limited to carbinolamine, disulfide, carbamide, aminal, carbonate, ester, carbamate, phosphate, amide, acetal, imine, oxime, ether, and sulfonamide groups; the non-cleavable linkers can be but not limited to alkyl and aryl groups.

Figure 2:
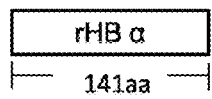
FIG. 2 depicts the amino acid sequence of different hemoglobin subunits ($\alpha$, $\beta$, $\gamma1$, $\gamma2$) of human origin (*Homo sapiens*) and the design for recombinant hemoglobin monomer (i.e., monomer $\alpha$, monomer $\beta$, monomer $\gamma1$, and monomer $\gamma2$), dimer (i.e., dimer $\alpha\beta$, dimer $\alpha\gamma1$, dimer $\alpha\gamma2$, dimer $\beta\gamma1$, and dimer $\beta\gamma2$) and tetramer (i.e., tetramer $2\alpha\beta_2$, tetramer $2\alpha\gamma1_2$, tetramer $2\alpha\gamma2_2$, tetramer $2\beta\gamma1_2$, tetramer $2\beta\gamma2_2$).
Figure 2:
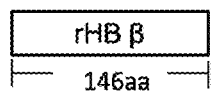
Figure 2:
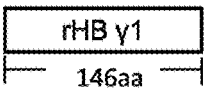
Figure 2:
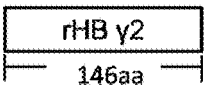
Figure 2:
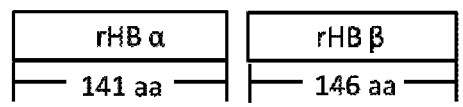
Figure 2:
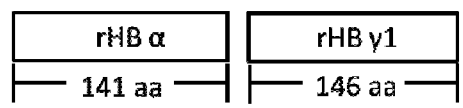
Figure 2:
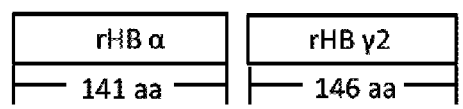
Figure 2:
Figure 2:
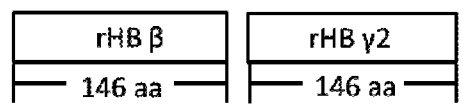
Figure 2:
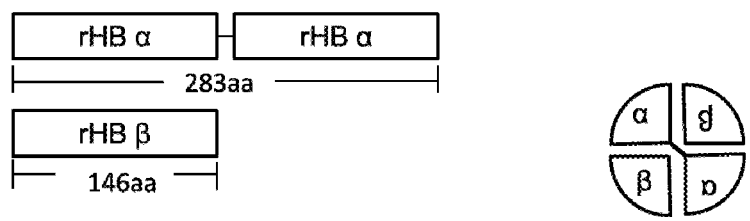
Figure 2:
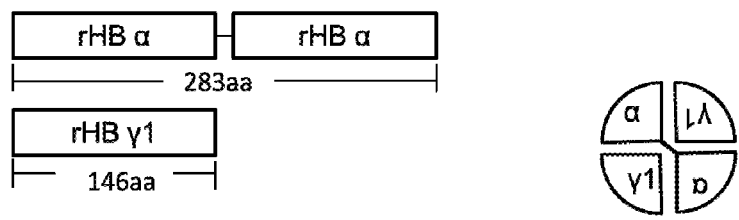
Figure 2:
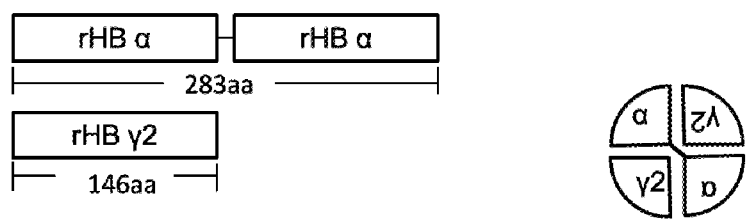
Figure 2:
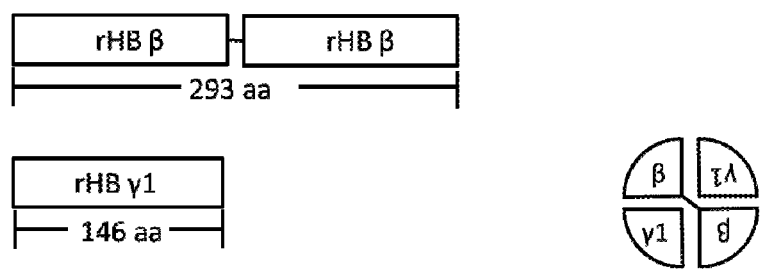
Figure 2:
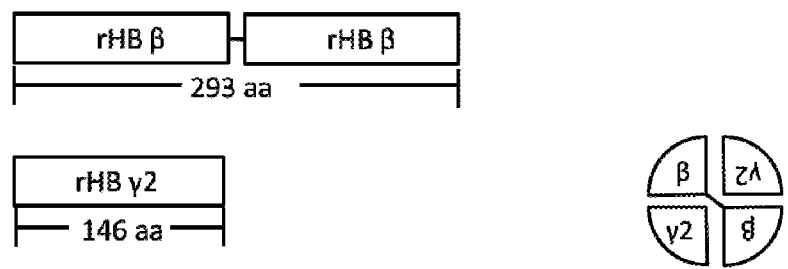

FIG. 2 shows the amino acid sequences alignment of different hemoglobin subunits (α, β, γ1, γ2) and the design of recombinant hemoglobin monomer, dimer and tetramer. The recombinant hemoglobin can be produced using sequences from various species including, but not limited to, human, bovine, porcine, equine, and canine hemoglobin. In this example, different Homo sapiens hemoglobin subunit amino acid sequences with about 141-146 amino acids, namely alpha, beta, gamma 1, and gamma 2 (SEQ ID Nos. 1 to 4), are selected for design of the DNA construct to be inserted into an expression vector and optionally tagged with His-sumo/Poly-His sequence for separation and purification after being expressed in a host (e.g., bacteria) which is transformed with the expression vector carrying the corresponding DNA construct. The process for producing the recombinant hemoglobin protein/subunits is outlined in the flow chart of FIG. 3. Any two of the subunits, e.g. alpha and beta subunits or alpha and gamma 1 subunits, can be expressed by using another expression vector carrying corresponding DNA sequences expressing alpha and beta subunits or alpha and gamma 1 subunits. After purification following the process illustrated in the flow chart of FIG. 3, dimers $\alpha\beta$, $\alpha\gamma1$, $\alpha\gamma2$, $\beta\gamma1$, and $\beta\gamma2$ can be formed, respectively. Further recombination of more than two subunits, e.g. two alpha subunits and two beta subunits, or two alpha subunits and two gamma-1 subunits, or two alpha subunits and two gamma-2 subunits, to form a tetramer, i.e. $2\alpha\beta_2$, $2\alpha\gamma1_2$, $2\alpha\gamma2_2$, $2\beta\gamma1_2$, $2\beta\gamma2_2$ respectively, can also be formed using similar approach. Further modification such as cross-linking between two hemoglobin subunits within the tetramer can be performed. Schematic diagram of the design of amino acid sequence(s) of the recombinant hemoglobin subunit, dimer, and tetramer is shown in FIGS. 2A, 2B, and 2C, respectively.

Figure 3:
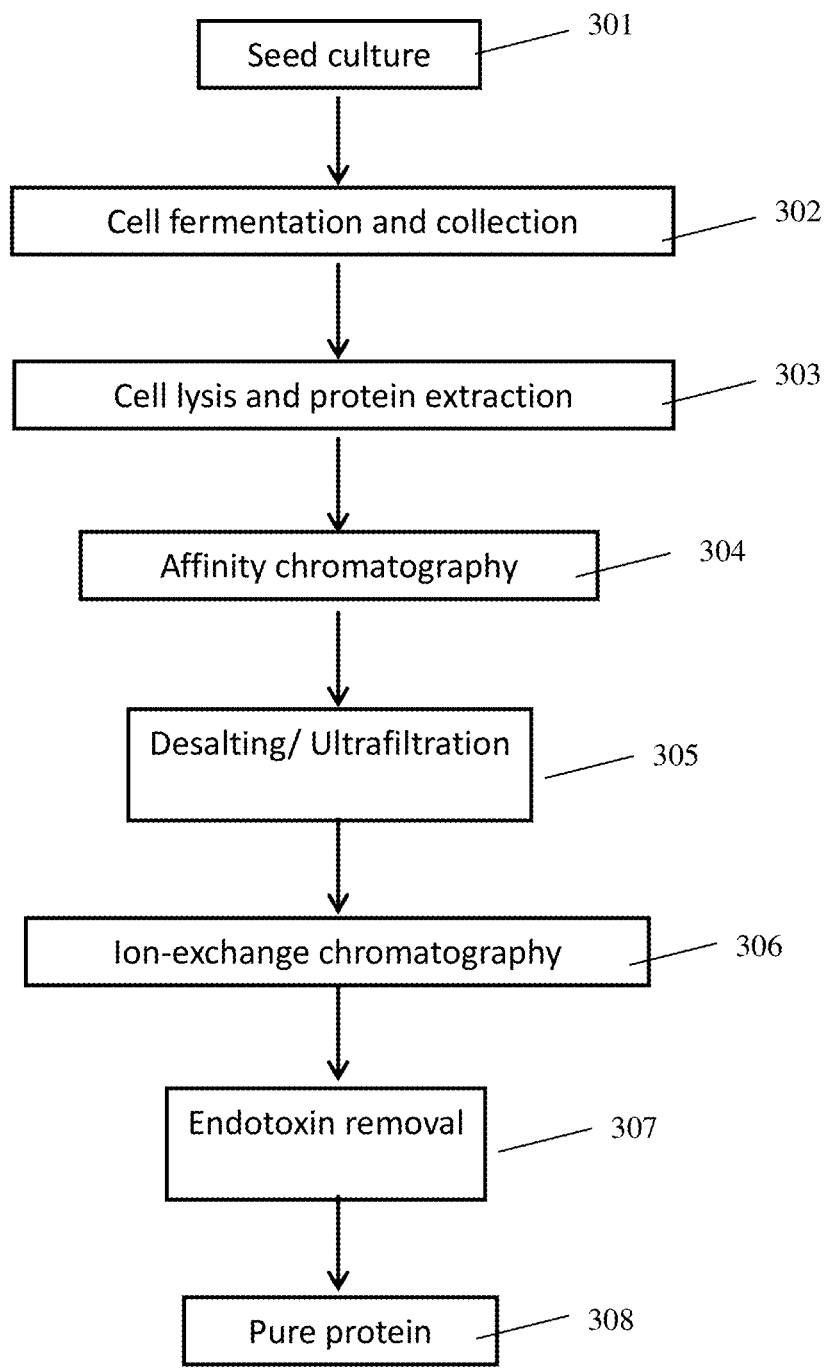
FIG. 3 is a flow chart depicting an overview of the method for preparing the recombinant hemoglobin protein or tetramer or dimer or subunit of the present invention from cells transformed with different constructs expressing the proteins of different hemoglobin tetramer, dimer or subunits with the amino acid sequence described herein.

Process depicted in FIG. 3 is based on a standard molecular chemistry technique for expressing a recombinant protein in a host system transformed with an expression vector design for carrying the corresponding DNA construct in order for expressing the corresponding hemoglobin subunit, dimer, or tetramer of the present invention. Other possible method which can express the recombinant protein can also be used for expressing the present recombinant hemoglobin protein/tetramer/dimer/subunit. Initially, a seed culture with transformed host cells carrying the DNA construct for expressing the corresponding hemoglobin subunit is prepared (301) for fermentation (302). The cells are harvested by centrifugation (302). The harvested cells are then lysed to isolate the crude protein (303). The crude protein is then purified using affinity chromatography (304). The salt in the eluate from the affinity chromatography is removed by a desalting column and/or ultrafiltration (305). The semi-purified protein is further purified by an ion-exchange column chromatography (306) in order to remove the protein impurities and endotoxin (307). The process of the present invention is applicable to large-scale industrial production of recombinant monomeric, dimeric and tetrameric hemoglobin. In addition, the recombinant hemoglobin protein/tetramer/dimer/subunit in combination with a pharmaceutical carrier (e.g. water, physiological buffer, in capsule) is suitable for mammalian use.

Figure 4:
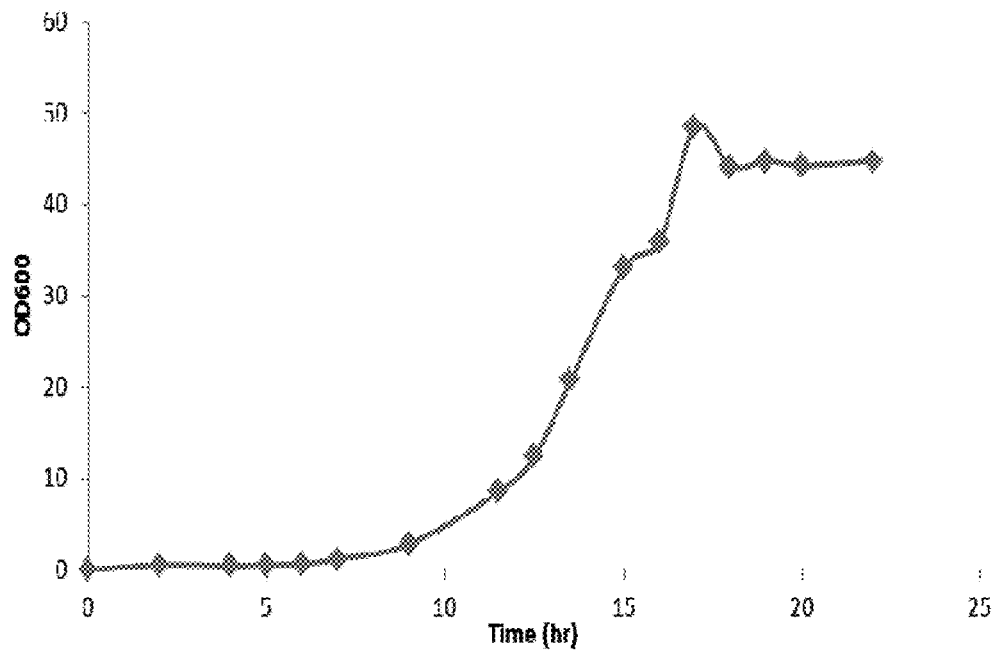
FIG. 4 shows the growth curve of *E. coli* cells JM109 (DE3) for the expression of recombinant hemoglobin subunit gamma-1 ($\gamma1$).
Figure 5:
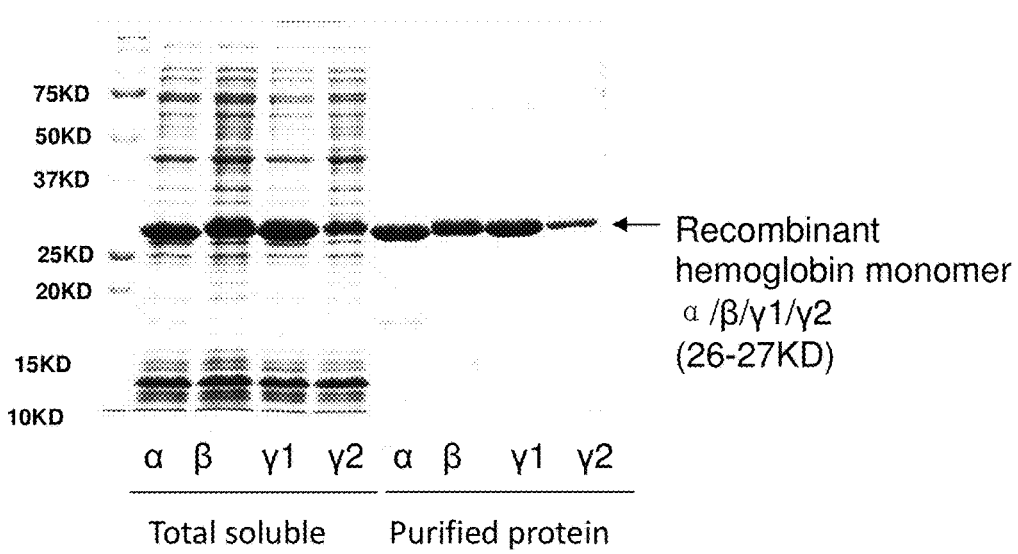
FIG. 5 shows molecular size of (A) purified recombinant hemoglobin subunits ($\alpha$, $\beta$, $\gamma1$, $\gamma2$) and (B) purified recombinant hemoglobin dimer and tetramer in SDS-PAGE.
Figure 5:
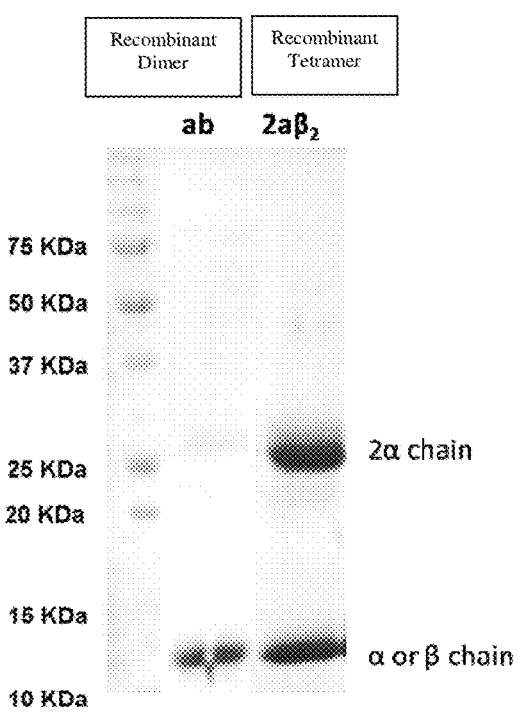
Figure 6:
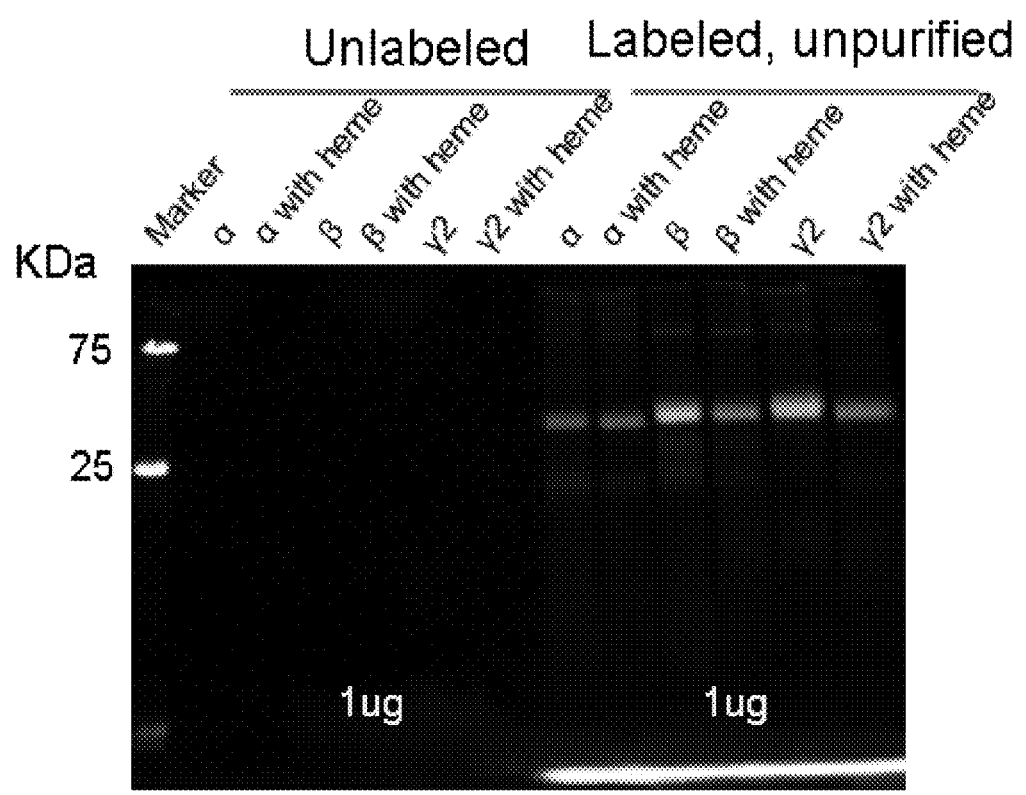
FIG. 6 shows the purified recombinant hemoglobin subunits ($\alpha$, $\beta$, $\gamma1$, $\gamma2$) with or without heme, labeled with fluorescent dyes.

The construction and expression of different recombinant hemoglobin proteins or recombinant hemoglobin subunits are carried out in *E. coli*. For example, *E coli* JM109 (DE3) transformed with expression vector carrying the DNA construct for expression of Gamma-1 ($\gamma1$) subunit are seeded and cultured for about 16 hours in order to harvest the cells for cell lysis and protein extraction. The growth curve of *E coli* JM109 (DE3) for expressing Gamma-1 ($\gamma1$) subunit is show in FIG. 4. The recombinant hemoglobin proteins/tetramer/dimer/subunits are then purified by column chromatography methods. The recombinant hemoglobin subunits ($\alpha$, $\beta$, $\gamma1$, $\gamma2$) expressed and purified according to the process of the present invention are shown in FIG. 5A and the recombinant hemoglobin dimer and tetramer expressed and purified according to the process of the present invention are shown in FIG. 5B. FIG. 6 shows that the unpurified but florescent labeled subunit with or without heme.

Figure 7:
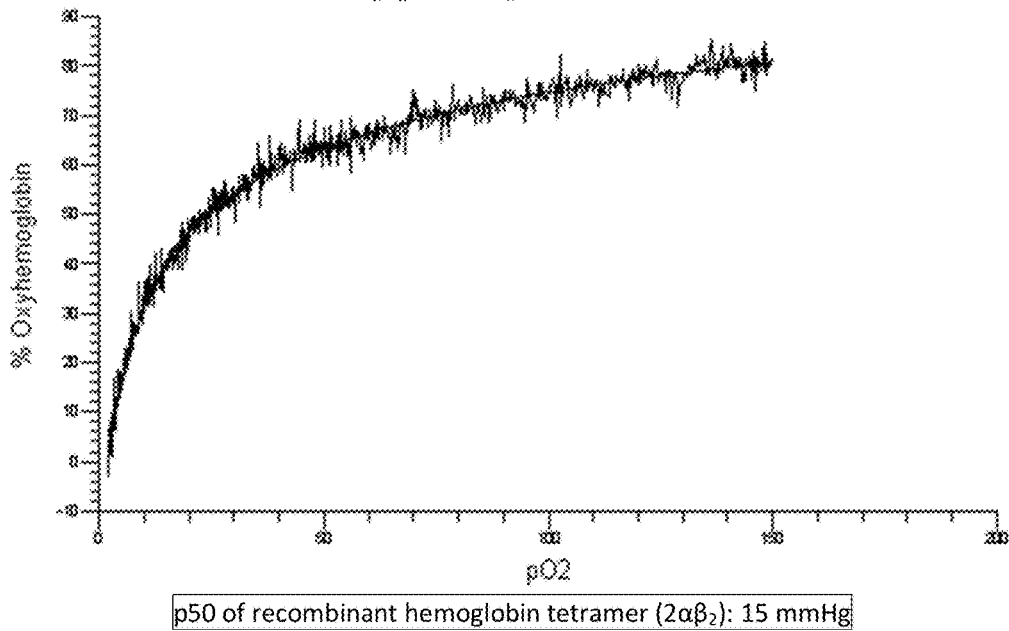
FIG. 7 shows the oxygen equilibrium curve for (A) one of the recombinant hemoglobin tetramer ($2\alpha\beta_2$) and another one of the recombinant hemoglobin tetramer ($2\alpha\gamma1_2$) of the present invention.
Figure 7:
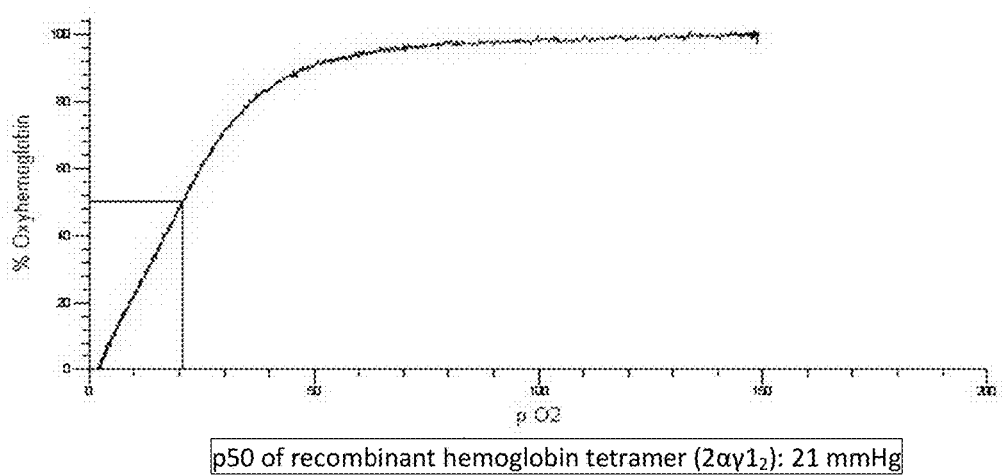

A p50 value of a test compound, meaning the oxygen partial pressure necessary to produce 50 percent saturation of hemoglobin in the present invention, is measured and the result is shown in FIG. 7. A native human hemoglobin has a p50 value on the order of approximately 23-30 mm Hg). FIG. 7 shows the oxygen equilibrium curve for (A) the recombinant hemoglobin tetramer ($2\alpha\beta_2$) and (B) the recombinant hemoglobin tetramer ($2\alpha\gamma1_2$). As shown in FIG. 7, the recombinant hemoglobin tetramer $2\alpha\beta_2$ has a p50 value on the order of ~15 mm Hg and the recombinant hemoglobin tetramer $2\alpha\gamma1_2$ has a p50 value on the order of ~21 mm Hg. Recombinant hemoglobin with a relatively higher oxygen affinity and a lower p50 value of less than approximately 23 mm Hg is formed, compared with native human hemoglobin which has a p50 value on the order of 23-30 mm Hg. Compositions containing hemoglobin-based oxygen carrier with lower oxygen affinity are used when rapid oxygenation is desired in cases of tissue hypoxia resulting from extensive blood loss (e.g., hemorrhagic shock). Lower oxygen affinity means that the material can "offload" oxygen to a target more easily than a material with a higher oxygen affinity. Compositions with higher oxygen affinity are useful as oxygenation adjunct therapies in cancer treatment where a slower delivery rate of oxygen is desired in that case.

For use in the treatment of oxygen-deprivation disorders and for heart preservation, the hemoglobin-based oxygen carrier-containing pharmaceutical composition with a lower oxygen affinity of the present invention provides oxygen to a target organ or subject. The present recombinant hemoglobin protein or tetramer or dimer or subunit with lower oxygen affinity is useful for applications requiring rapid tissue oxygenation (e.g. hemorrhagic shock and ex vivo organ preservation).

For applications in cancer treatment, the hemoglobin-based oxygen carrier-containing pharmaceutical composition with a higher oxygen affinity of the present invention serves as a tissue oxygenation agent to improve the oxygenation in tumor tissues, thereby enhancing chemo- and radiation sensitivity. The present recombinant hemoglobin with a relatively higher oxygen affinity is useful for applications requiring a slower rate of oxygenation (e.g. cancer adjunct therapy).

Figure 8:
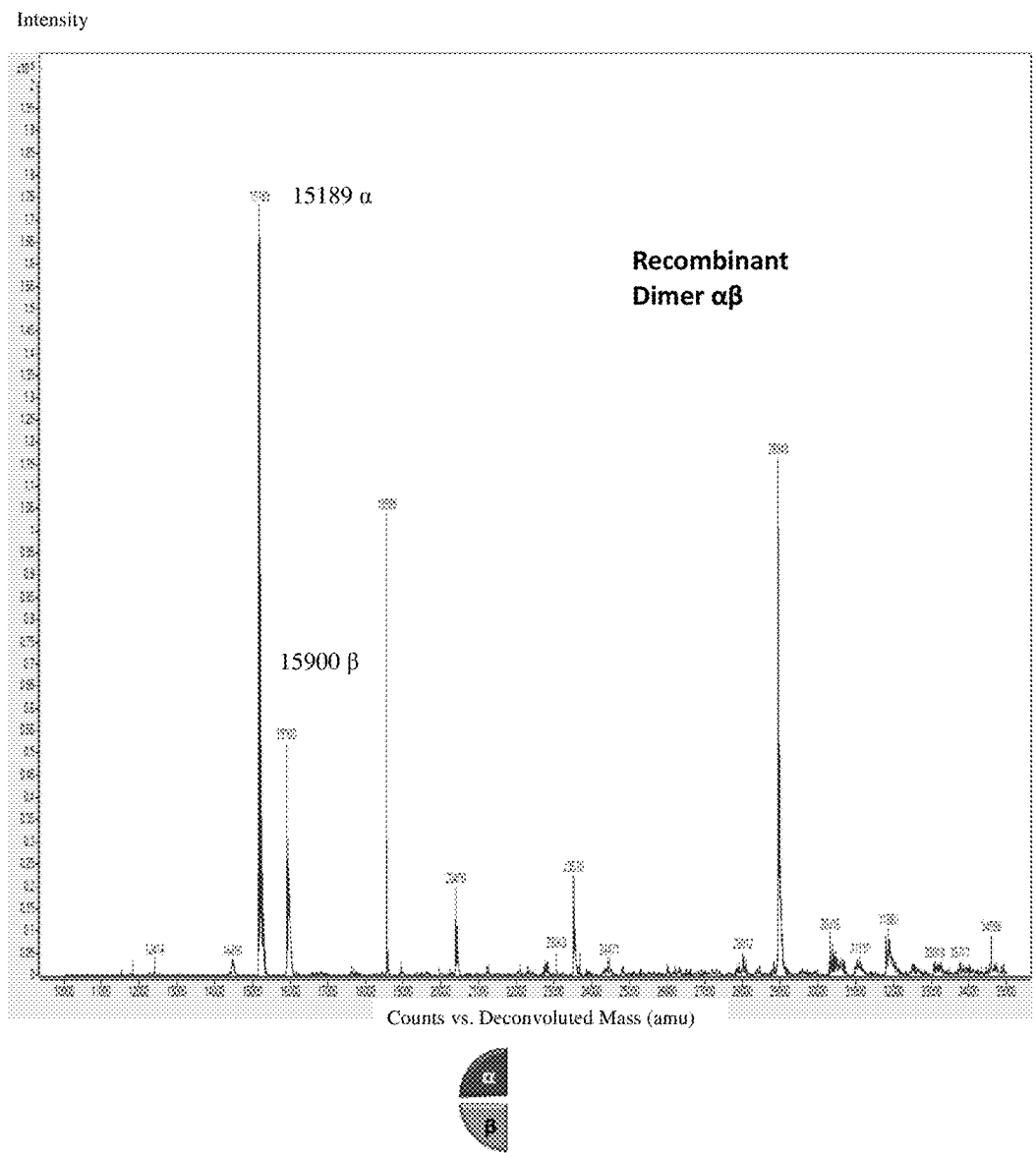
FIG. 8 depicts electrospray ionization mass spectrometry (ESI-MS) analysis for one of the recombinant hemoglobin dimers of the present invention ($\alpha\beta$).
Figure 9:
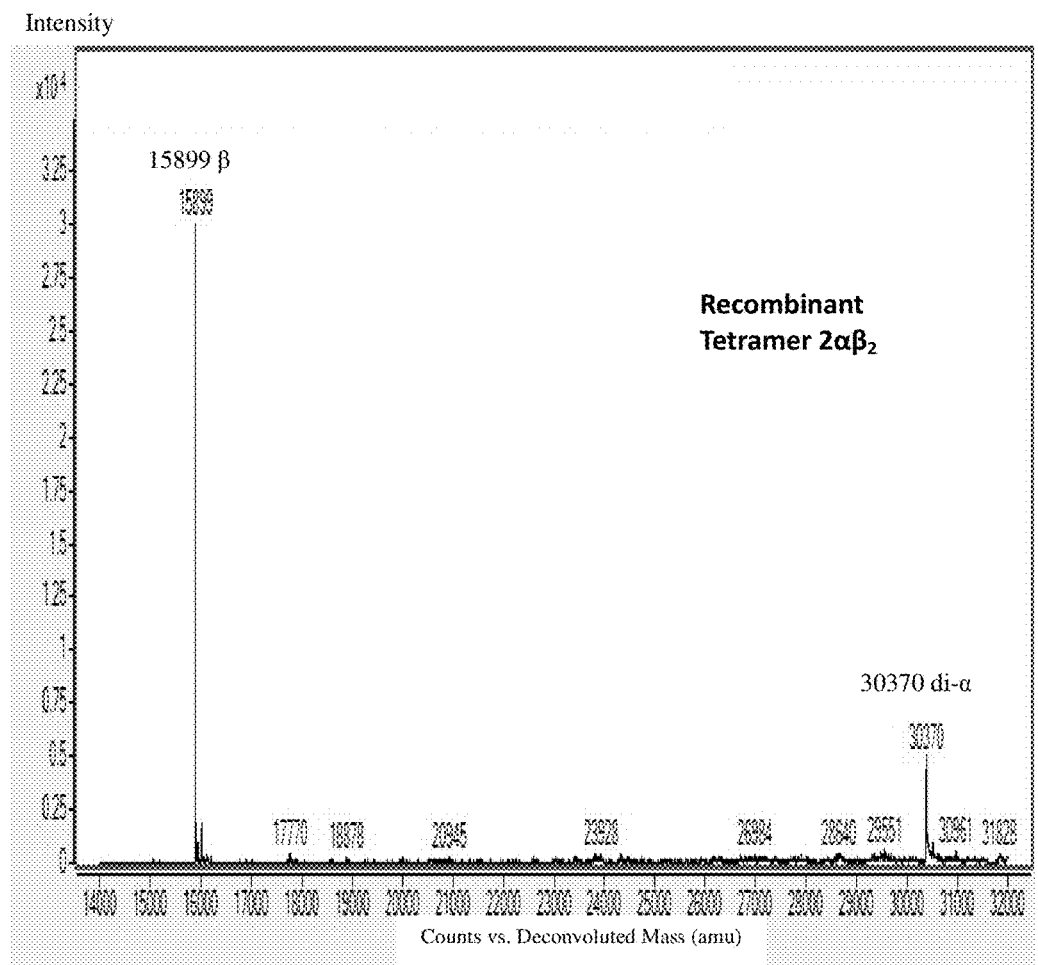
FIG. 9 depicts electrospray ionization mass spectrometry (ESI-MS) analysis for one of the recombinant hemoglobin tetramers of the present invention ($2\alpha\beta_2$).
Figure 9:
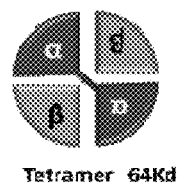
Figure 9:
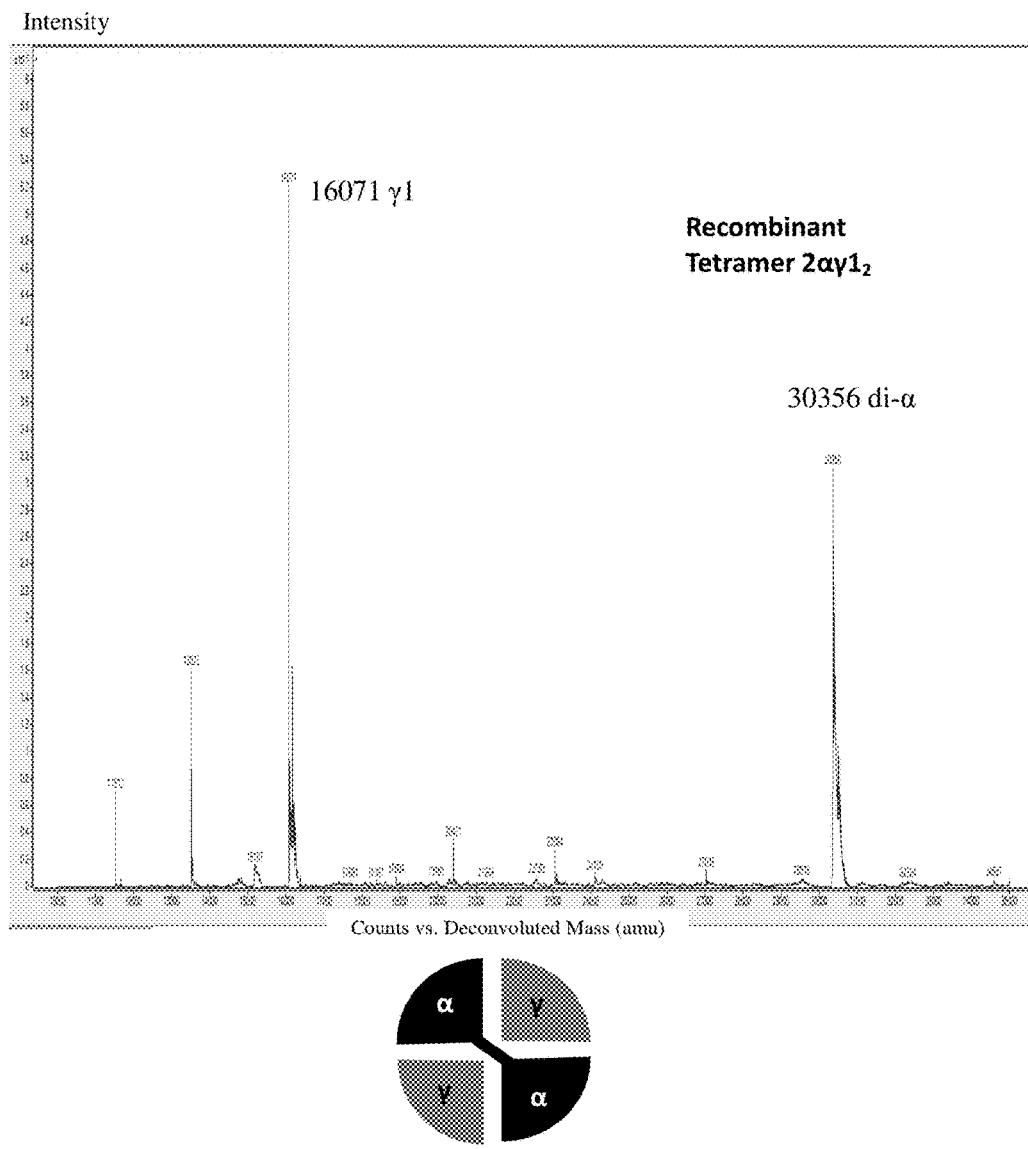

ESI-MS allows the analysis of very large molecules. It is an ionization technique that analyzes the high molecular weight compound by ionizing the protein, and then separating the ionized protein based on mass/charge ratio. Therefore, the molecular weight and the protein interactions can be determined accurately. An electrospray ionization mass spectrometry (ESI-MS) is used to analyze and characterize the recombinant hemoglobin monomer, dimer and tetramer in this invention. FIG. 8 depicts electrospray ionization mass spectrometry (ESI-MS) analysis for the recombinant hemoglobin dimer ($\alpha\beta$). The size of $\alpha$ subunit is 15,189 Da and the size of $\beta$ subunit is 15,899 Da. FIG. 9 depicts electrospray ionization mass spectrometry (ESI-MS) analysis for the recombinant hemoglobin tetramer ($2\alpha\beta_2$). The size of $\beta$ subunit is 15,899 Da and the size of $2\alpha$ is 30,356 Da. From this analysis, the estimated total molecular size of $2\alpha\beta_2$ is about 46 KDa. ESI-MS also performs for the recombinant hemoglobin tetramer ($2\alpha\gamma1_2$), other recombinant hemoglobin dimer and monomer.

The recombinant hemoglobin protein/tetramer/dimer/subunit of the present invention is used to produce medicaments for tissue oxygenation, for cancer treatment, for the treatment of an oxygen-deprivation disorder such as hemorrhagic shock, and in heart preservation under a low oxygen content environment (e.g. heart transplant). The dosage of recombinant hemoglobin tetramer of the present invention is selected at a concentration range of approximately 0.03 g/kg or less of an animal's body weight or 0.0024 g/kg or less of a human's body weight (human dose is determined by dividing the dose for mouse by a coefficient of 12.3 according to a FDA guidance for industry and reviewers: Estimating the Safety Starting Dose in Clinical Trials for Therapeutics in Adult Healthy Volunteers, Nov. 18, 2002).

For a medicament useful in cancer treatment, the hemoglobin-based oxygen-carrier-containing pharmaceutical composition of the present invention serves as a tissue oxygenation agent to improve the oxygenation in tumor tissues, thereby enhancing chemo-sensitivity (e.g., sensitivity to chemotherapy) and radiation sensitivity.

Figure 10:
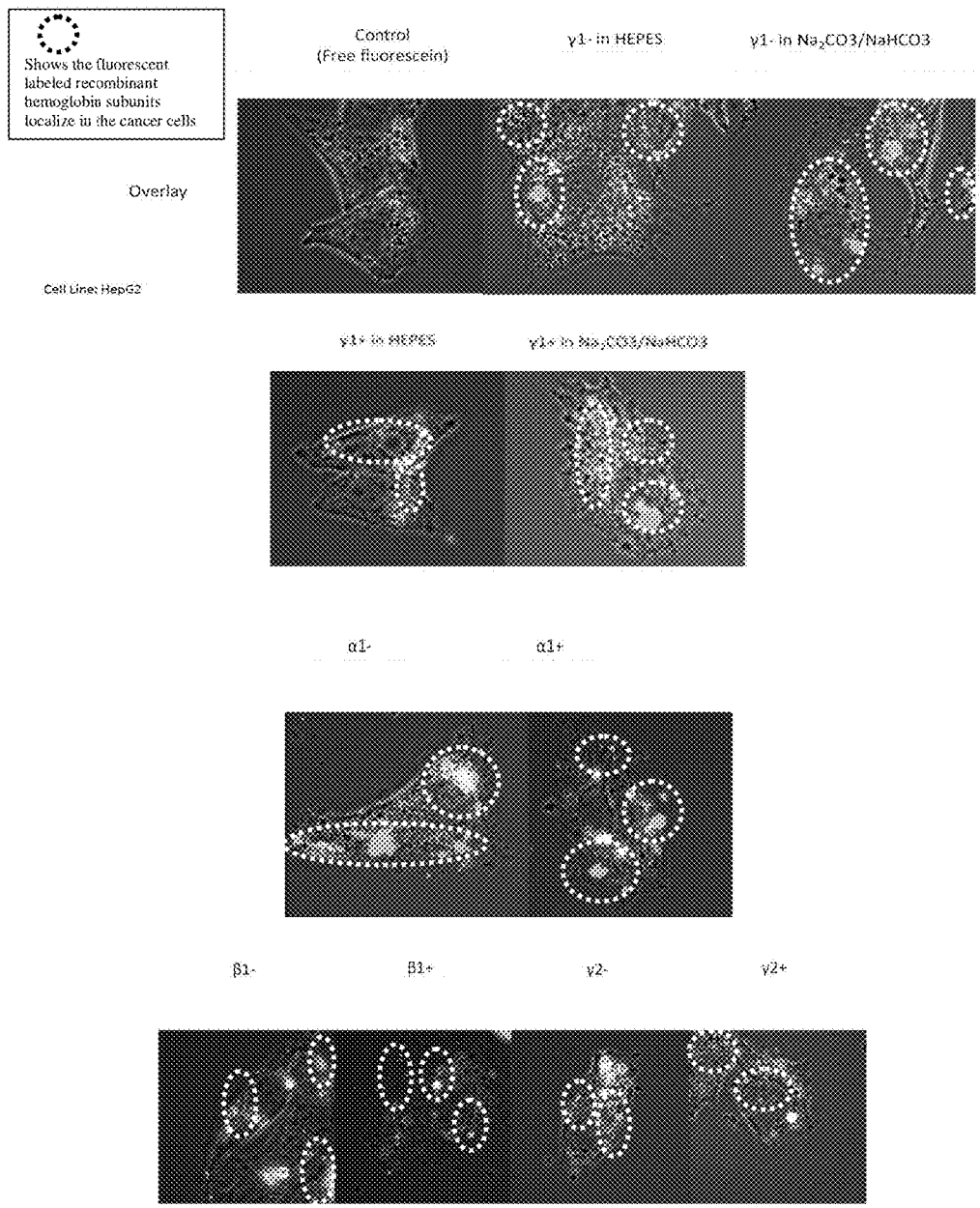
FIG. 10 illustrates that the fluorescent labeled recombinant hemoglobin subunits ($\alpha$, $\beta$, $\gamma1$, $\gamma2$) with heme (+) or without heme (−) can enter into liver cancer cells (HepG2) successfully.

The pharmaceutical composition of the present invention comprises recombinant hemoglobin protein or recombinant hemoglobin tetramer or dimer or subunit-based therapeutic agent capable of both targeting and killing the cancer cells. FIG. 6 shows the purified recombinant hemoglobin subunits ($\alpha$, $\beta$, $\gamma 1$, $\gamma 2$) with or without heme, labeled with fluorescent dyes. The fluorescent labeled recombinant hemoglobin subunits can also enter into the cancer cells (e.g., liver cancer cells, HepG2) and localize in there, and the result is illustrated in FIG. 10. It is expected that the chemically modified recombinant hemoglobin protein or tetramer or dimer or subunit-based therapeutic agent can also kill the cancer cells and progenitor cells/cancer stem cells effectively.

Figure 11:
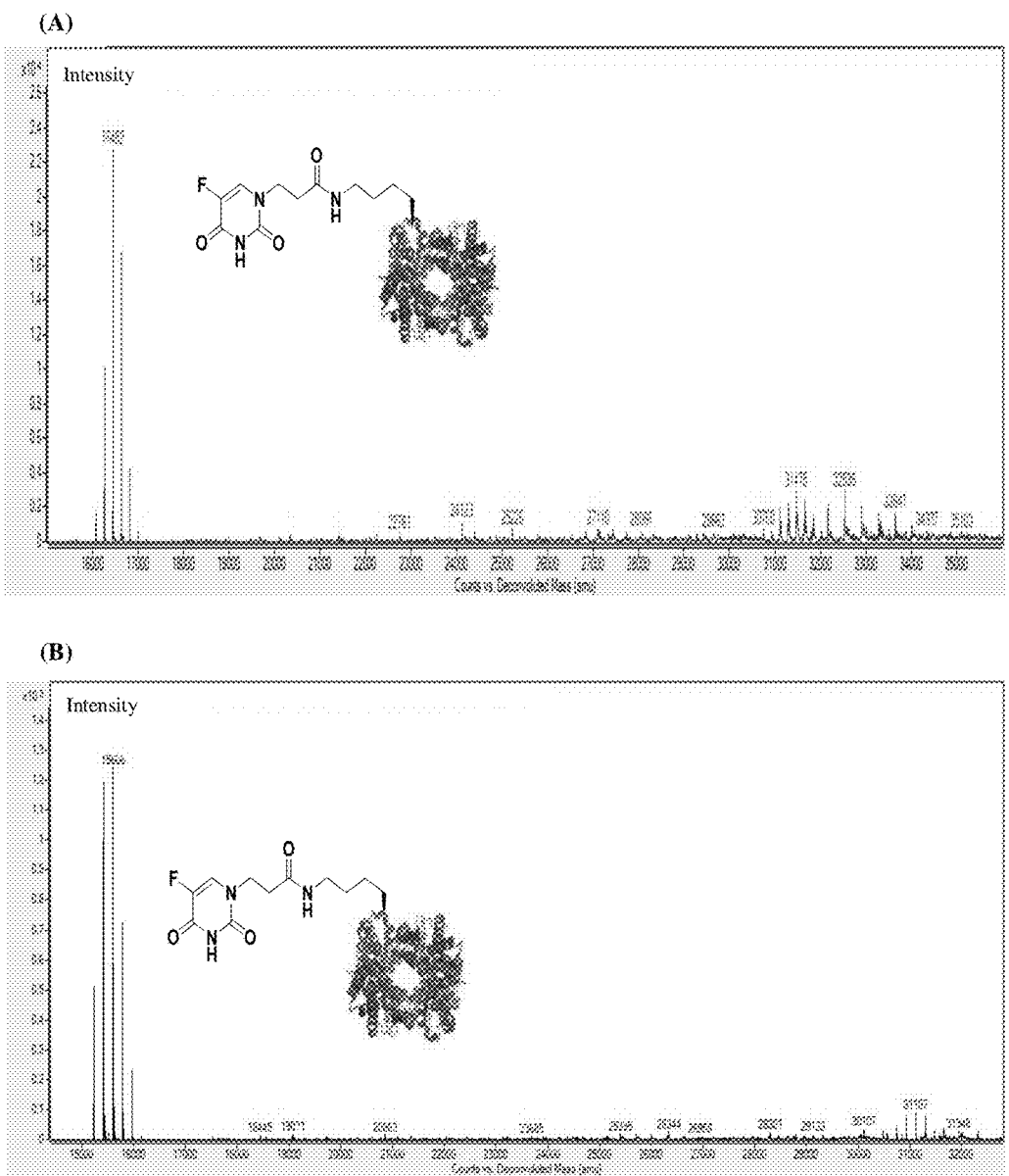
FIG. 11 shows the liquid chromatography-mass spectrometry (LC-MS) results for (A) 5FU-linked recombinant hemoglobin tetramer ($2\alpha\beta_2$) and (B) 5FU-linked recombinant hemoglobin tetramer ($2\alpha\gamma1_2$).

Some conventional therapeutic drugs (e.g. chemotherapeutic drug, 5FU) cannot be used in high dose because of high toxicity. In the present invention, the chemotherapeutic agent, e.g., 5FU, is chemically linked to the recombinant hemoglobin protein or recombinant hemoglobin tetramer or dimer or any of the subunits thereof or the recombinant hemoglobin subunit itself. The chemotherapeutic agent linked to the presently claimed recombinant hemoglobin protein or tetramer or dimer or the subunit thereof can be lower in dose than other conventional method/agents for cancer being administered alone because the presently claimed recombinant hemoglobin protein or tetramer or dimer or subunit facilitates localization of the chemotherapeutic agent in the cytoplasm of the cancerous cells in order to increase the efficacy of both the recombinant hemoglobin protein or tetramer or dimer or subunit of the present invention and the chemotherapeutic agent. The recombinant hemoglobin protein or tetramer or dimer or subunit of the present invention can also improve the efficacy of the radiotherapeutic agent and/or other anti-cancer drugs on cancer cells or tumor, especially on those which is/are hypoxic that is more resistant to these conventional therapeutic drug for cancer treatment. FIG. 11 shows the liquid chromatography-mass spectrometry (LC-MS) results for (A) 5FU-linked recombinant hemoglobin tetramer ($2\alpha\beta_2$) and (B) 5FU-linked recombinant hemoglobin tetramer ($2\alpha\gamma 1_2$). 5FU is chemically linked successfully to the recombinant hemoglobin tetramer. It also applies to the other chemically linked recombinant hemoglobin dimer and recombinant hemoglobin subunit (or monomer).

The recombinant hemoglobin protein or tetramer or dimer or its subunit can be modified chemically by different functional groups before linking to the therapeutic drug. The recombinant hemoglobin protein or tetramer or dimer or its subunit can be modified by one or more of the following compound(s) or reaction(s): (1) for amine reactions: anhydride, ketene, NHS ester, isothiocyanates, isocyanates, activated esters which include fluorophenyl esters and carbonyl azides, sulfonyl chlorides, carbonyls followed by reductive amination, epoxides, carbonates, fluorobenzenes, imidoesters, hydroxymethyl phosphine derivatives, mannich condensation, diazonium derivatives, 4-sulfo-2,3,5,6-tetrafluorophenol, carbonyl diimidazole, sulfo-NHS, and N-terminal modification by pyridoxal-5-phoshpate-based biomimetic transamination; (2) for thiol reactions: maleimides, alkyl halides, haloacetamides, disulfides, thiosulfates, aziridine-containing reagents, acryloyl derivatives, arylating agents, and vinylsulfone derivatives; (3) for carboxylate reactions: diazoalkanes and diazoacetyl compounds, carbonyldiimidazoles, and carbodiimides; (4) for hydroxyl reactions: epoxides and oxiranes, carbonyldiimidazoles, carbonates, chloroformates, chemical and enzymatic oxidations, alkyl halogens, and isocyanates; (5) for native chemical ligations using thioesters; (6) N-terminal modification using periodate oxidation of N-terminal serine or threonine to generate aldehydes for coupling with hydroxylamines, hydrazines, or hydrazides, carbodiimides; (7) for incorporation of bioorthogonal functionalities: including alkynes and azides with subsequent bioorthogonal conjugation reactions which include dipolar addition Huisgen 1,3-dipolar additions of alkynes and azides, Staudinger ligation of azides and triarylphosphines, Diels-alder reaction of alkenes and tetrazines, and coupling of alkenes and tetrazoles; (8) for photochemical reactions: photoaffinity labeling agents, diazirine derivatives, benzophenones and anthraquinones; (9) for metal-mediated reactions: metal carbenoids and palladium-activated allyl reagents.

Figure 12:
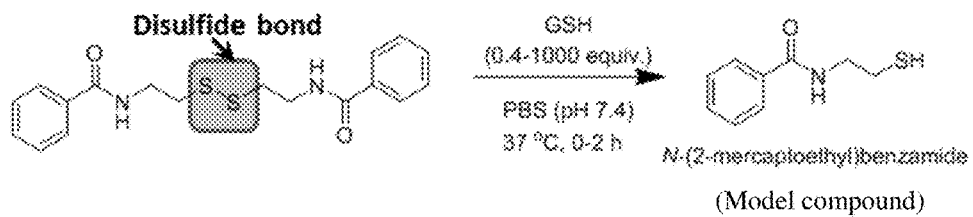
FIG. 12 shows (A) the cleavage of N-(2-mercaptoethyl) benzamide (model compound) with disulfide bond under reducing condition (i.e., GSH (0.4-1,000 equiv.); PBS (pH 7.4); 37° C., 0-2 hrs) and (B) the conversion rate of the model compound at different GSH levels: GSH (1 equiv.) is similar to that in blood stream while GSH (1,000 equiv.) is similar to that in cytoplasm.
Figure 12:
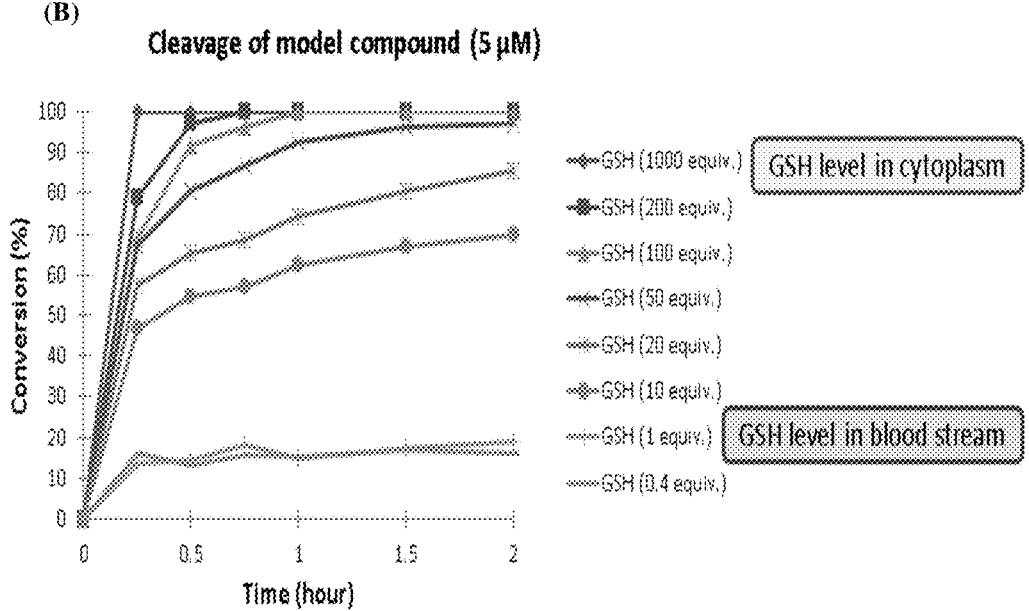

The glutathione (GSH) level is much higher in the cytoplasm of cancer cells (~1000 equiv) when compared to blood stream (~1 equiv). A therapeutic drug with a disulfide bond can be cleaved much more easily in the cytoplasm of cancer cells with high concentration of GSH. A high-performance liquid chromatography (HPLC) analysis for the cleavage of model compound (N-(2-mercaptoethyl)benzamide) with disulfide bond under reducing condition is shown in FIG. 12. The cleavage of model compound is observed in PBS buffer (pH 7.4) at 37° C. with different concentration of glutathione (GSH) (0.4-1000 equiv). The cleavage of the model compound is better at high concentration of GSH (>50 equiv). In the present invention, the recombinant hemoglobin protein or recombinant hemoglobin tetramer or dimer or subunit linked with a therapeutic drug (e.g. chemotherapeutic agent, radiotherapeutic agent, anti-cancer protein drug) by a disulfide bond is prepared for cancer treatment.

No recombinant hemoglobin protein or recombinant hemoglobin tetramer or dimer or subunit-based therapeutic agent is available in the market. The chemically modified recombinant hemoglobin protein or recombinant hemoglobin tetramer or dimer or subunit-based therapeutic agent-containing pharmaceutical composition provided in the present invention can target cancer cells with therapeutic effect. For uses in cancer treatment, the chemically modified recombinant hemoglobin protein or recombinant hemoglobin tetramer or dimer or subunit-based therapeutic agent-containing pharmaceutical composition of the present invention serves as an anti-cancer agent to kill cancer cells. The chemically modified recombinant hemoglobin protein or recombinant hemoglobin tetramer or dimer or subunit-based therapeutic agent is a good candidate to be used in lower dose and can be combined with other molecular targeting or cytotoxic agents.

EXAMPLES

The following examples are provided by way of describing specific embodiments of this invention without intending to limit the scope of this invention in any way.

Example 1

(a) Construction of Expression Vector with Recombinant Hemoglobin Protein and/or Tetramer and/or Dimer and/or its Subunit The DNA sequences of α/β/γ1/γ2 chain of human origin are synthesized and cloned in PUC 57 vector. The α/β/γ1/γ2 chains are amplified by PCR method. The primers used in PCR are designed based on both α/β/γ1/γ2 chains. A PCR is conducted in the Gradient Thermal Cycler (Life sci). The reaction is performed in a 25 ul reaction mixture containing Taq Buffer, 10 mM dNTP, 25 mM $MgCl_2$, 10 uM of primer, 2.5 U of Taq DNA polymerase and 100 ng of template DNA. The gradient PCR condition is comprised of an initial denaturation step of 3 min at 95° C. followed by 25 cycles of amplification consisting of denaturation at 95° C. for 30 s, primers annealing at 50-55° C. for 30 s and extension at 72° C. for 45 s prior to a final extension of 5 min at 72° C. The PCR products are separated by 1.5% agarose gel electrophoresis along with standard marker and stained with gel red. The product band of the expected size is excised and DNA fragment is extracted with the PCR clean-up Gel extraction kit following the manufacturer's instructions. The purified DNA fragment is cloned into a pSumo vector or PUC 19 vector. Ligation mixture is transformed into E. coli DH5a strain, and the transformants are selected on LB agar containing 100 ng/ml ampicillin. The putative clones are verified by nucleotide sequencing. Analysis of cDNA sequences is performed using BLAST algorithm program.

(b) Different Recombinant Hemoglobin Protein and/or Tetramer and/or Dimer and/or Subunits Seven recombinant hemoglobin protein and/or tetramer and/or dimer and/or subunits are generated as shown in FIG. 2 and Table 1. The protein sequences of α/β/γ1/γ2 chains are shown in FIG. 2. For recombinant hemoglobin monomers, α/β/γ1/γ2 chains are cloned into pSumo vector and the fusion protein expression are controlled by T7 promoter. For recombinant hemoglobin heterodimer, the α chain and β/γ1 chain are co-expressed in pUC19 vector and under the control of pTac promoter. For recombinant hemoglobin tetramer, the two α chain are linked by a glycine linker and co-expressed with β/γ1 chain in pUC19 vector and under the control of pTac promoter.

TABLE 1

Different recombinant hemoglobin protein and/or tetramer and/or dimer and/or subunits

| Numbering in FIG. 2 | Recombinant | Expressed hemoglobin subunit/chain/dimer/tetramer |
|---|---|---|
| #1 | Monomer | α (141 amino acids) |
| #2 | | β (146 amino acids) |
| #3 | | γ1 (146 amino acids) |
| #4 | | γ2 (146 amino acids) |
| #5 | Dimer | αβ (287 amino acids) |
| #6 | | αγ1 (287 amino acids) |
| #7 | | αγ2 (287 amino acids) |
| #8 | | βγ1 (292 amino acids) |
| #9 | | βγ2 (292 amino acids) |
| #10 | Tetramer | $2αβ_2$ (575 amino acids) |
| #11 | | $2αγ1_2$ (575 amino acids) |
| #12 | | $2αγ2_2$ (575 amino acids) |
| #13 | | $2βγ1_2$ (585 amino acids) |
| #14 | | $2βγ2_2$ (585 amino acids) |

Example 2

Recombinant Protein Expression

The plasmids for expression of recombinant hemoglobin protein/tetramer/dimer/subunit are transformed into E. coli JM109(DE3) or E. coli BL21(DE3). E. coli cells are grown in LB medium supplemented with ampicillin (100 mg/ml) at 37° C. For shake flask expression, overnight cultures are 1:100 added into LB medium contained 100 mg/ml ampicillin. The cells are grown in a shake flask at 37° C. until the optical density at 600 nm reached 0.6. Expression of recombinant hemoglobin protein/tetramer/dimer/subunit is induced by adding isopropyl b-thiogalactopyranoside to 0.4 mM. The culture is then supplemented with hemin (20 mg/L) and the growth is continued for at least 16 h at 28° C. For fermenter cultures, medium used for the expression of recombinant hemoglobin protein/tetramer/dimer/subunit contained 1.28% bactotryptone, 0.8% bactoyeast extract, 1% glycerol, 25 mM $KH_2PO_4$, 25 mM $Na_2HPO_4$, 45 mM $NH_4Cl$, 5 mM $(NH4)_2SO_4$ and 100 mg/L ampicillin. The cells are grown in a 2 L fermenter (Sartorius, BIOSTAT® B) at 30° C. until the optical density at 600 nm reached 8. Expression of recombinant hemoglobin protein/tetramer/dimer/subunit is induced by adding isopropyl b-thiogalactopyranoside (Sigma) to mM. The culture is then supplemented with hemin (50 mg/L) and the growth is continued for at least 16 h at 25° C. The cells are harvested by centrifugation and stored frozen at −80° C. until needed for purification.

Example 3

Protein Yield for Recombinant Hemoglobin in Shake Flasks and Fermentor

The protein yield of recombinant hemoglobin protein and/or tetramer and/or dimer and/or subunit is summarized in Table 2. The protein yield from fermentation method is much higher, can be up to 180 mg/L.

TABLE 2

Protein yield of recombinant human hemoglobin by shaking flask and fermentation.

| Protein | Culture method | Protein yield |
|---|---|---|
| Monomer - α | Shake flask | 20-40 mg/L |
| Monomer - β | Shake flask | 20-40 mg/L |
| Monomer - γ1 | Shake flask | 20-40 mg/L |
| Monomer - γ2 | Shake flask | 20-40 mg/L |
| Dimer - αβ | Shake flask | 5-10 mg/L |
| Dimer - αγ1 | Shake flask | 5-10 mg/L |
| Tetramer - $2αβ_2$ | Shake flask | 5-10 mg/L |
| Monomer - γ1 | Fermentation | 180 mg/L |
| Tetramer - $2αβ_2$ | Fermentation | 30-40 mg/L |

Example 4

Culture and Reagents for Cancer Cell Line

Cancer cells (HepG2) are cultured in DMEM (Invitrogen) with 10% Fetal bovine serum (FBS), 100 U/mL penicillin and 100 µg/mL streptomycin at 37° C. For normoxic condition, cells are incubated with ambient $O_2$ concentration and 5% $CO_2$; for hypoxic condition, cells are incubated with 0.1-0.5% $O_2$ (Quorum FC-7 automatic $CO_2/O_2/N_2$ gas mixer) and 5% $CO_2$.

Example 5

Live Cell Time-Lapse Microscopy in Cancer Cells

Cancer cells (e.g. HepG2 liver cancer cells) are seeded onto glass bottom microwell dishes (MatTek Corporation). Live cells at defined zooms (63×, 20×) are acquired using Zeiss Observer Z1 widefield microscope, equipped with atmospheric/temperature-controlled chamber and motorized stage for multi-positional acquisition. The incubation is performed in an enclosed live cell imaging system purged with 0.1% $O_2$ and 5% $CO_2$ (premixed). Cells are exposed to the fluorescent labeled recombinant hemoglobin subunits (α, β, γ1, γ2); for 15 min prior to the acquisition of images every 3 min for a period of 2 h. Images are deconvolved and compacted into time-lapse movies using the MetaMorph software (Molecular Device). The images are shown in FIG. 10.

Example 6

Figure 13:
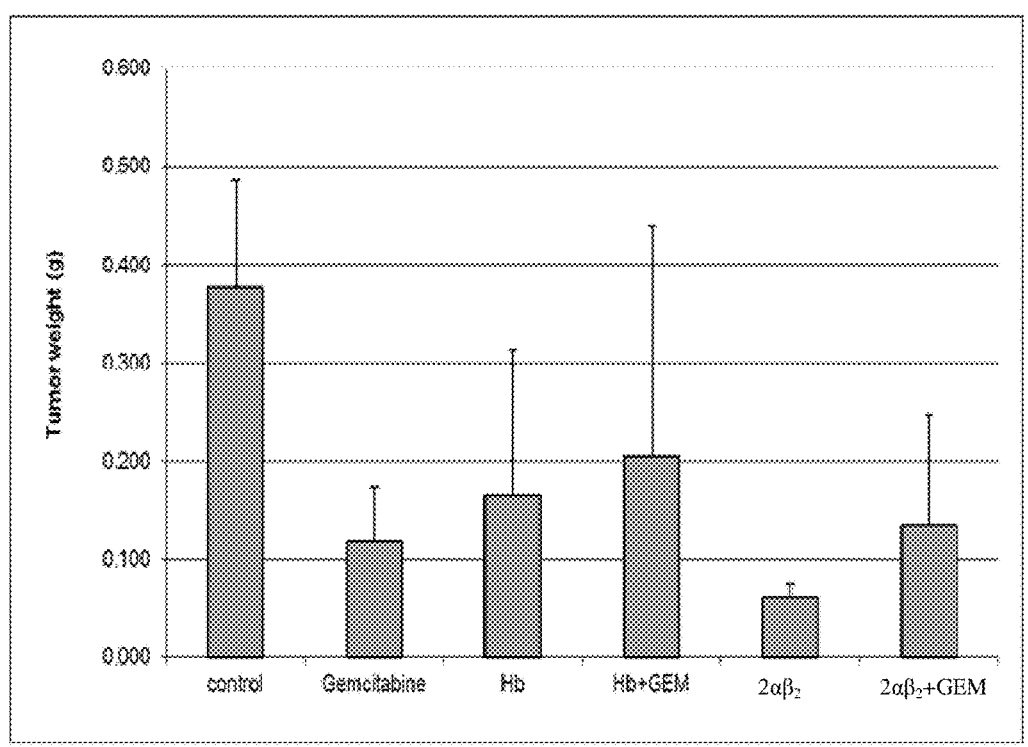
FIG. 13 shows the efficacy of native bovine crosslinked hemoglobin (Hb) tetramer and recombinant hemoglobin tetramer of the present invention ($2\alpha\beta_2$) with or without Gemcitabine (GEM) in reducing tumor size in terms of the tumor weight (g) in a pancreatic cancer Capan-1 animal model as compared to a control and a group of animal model treated with GEM only; Group 1: PBS buffer (Control); Group 2: Gemcitabine (GEM), 100 mg/kg; Group 3: Native bovine crosslinked hemoglobin (Hb) tetramer, 30 mg/kg; Group 4: Native bovine crosslinked hemoglobin tetramer+Gemcitabine (Hb+GEM); Group 5: Recombinant hemoglobin tetramer ($2\alpha\beta_2$), 30 mg/kg; Group 6: Recombinant hemoglobin tetramer ($2\alpha\beta_2$)+Gemcitabine.

(a) In Vivo Efficacy of Recombinant Hemoglobin Tetramer ($2\alpha\beta_2$) on Cancer Cell Xenografts Nude balb/c mice (5-7 weeks) are used in this example and they are allowed to acclimatize for a week before the experiment. Mice are inoculated subcutaneously with $2\times10^6$ cancer cells in 100 μl of fresh culture medium. Ten days later, the mice are randomly separated into control and treatment group. Control group receives 100 μl PBS and treatment group (Group 2-6) receives the drug intraperitoneally weekly (twice per week, for 4 weeks). Gemcitabine is an anti-cancer ("antineoplastic" or "cytotoxic") chemotherapy drug, and it is used in Group 2, Group 4 & Group 6. Tumor size is measured by caliper and tumor volume is calculated using formula: (length×width2)/2. The result is shown in FIG. 13. The result shows that the recombinant hemoglobin tetramer ($2\alpha\beta_2$) can inhibit the growth of tumor cells.

Figure 14:
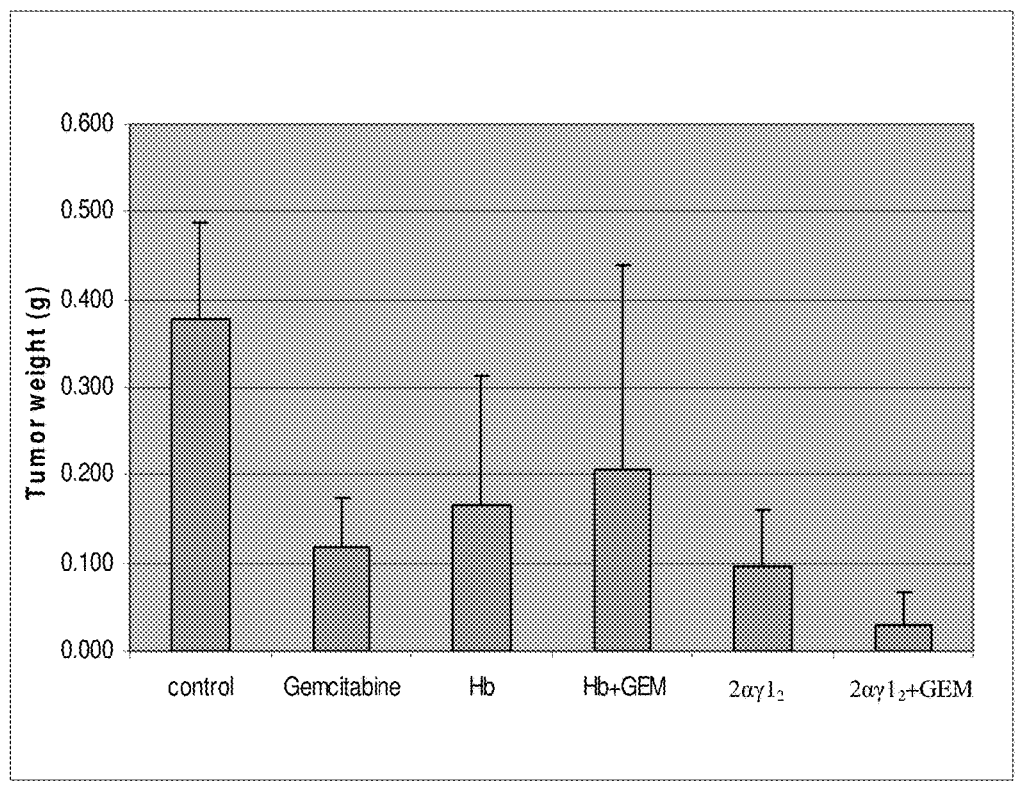
FIG. 14 shows the efficacy of native bovine crosslinked hemoglobin (Hb) tetramer and recombinant hemoglobin tetramer of the present invention ($2\alpha\gamma1_2$) with or without Gemcitabine (GEM) in reducing tumor size in terms of the tumor weight (g) in a pancreatic cancer Capan-1 animal model as compared to a control and a group of animal model treated with GEM only; Group 1: PBS buffer (Control); Group 2: Gemcitabine (GEM), 100 mg/kg; Group 3: Native bovine crosslinked hemoglobin (Hb) tetramer, 30 mg/kg; Group 4: Native bovine crosslinked hemoglobin tetramer+Gemcitabine (Hb+GEM); Group 5: Recombinant hemoglobin tetramer ($2\alpha\gamma1_2$), 30 mg/kg; Group 6: Recombinant hemoglobin tetramer ($2\alpha\gamma1_2$)+Gemcitabine.

(b) In Vivo Efficacy of Recombinant Hemoglobin Tetramer ($2\alpha\gamma1_2$) on Cancer Cell Xenografts Nude balb/c mice (5-7 weeks) are used in this example and they are allowed to acclimatize for a week before the experiment. Mice are inoculated subcutaneously with $2\times10^6$ cancer cells in 100 μl of fresh culture medium. Ten days later, the mice are randomly separated into control and treatment group. Control group receives 100 μl PBS and treatment group (Group 2-6) receives the drug intraperitoneally weekly (twice per week, for 4 weeks). Gemcitabine is an anti-cancer ("antineoplastic" or "cytotoxic") chemotherapy drug, and it is used in Group 2, Group 4 & Group 6. Tumor size is measured by caliper and tumor volume is calculated using formula: (length×width2)/2. The result is shown in FIG. 14. The result shows that the recombinant hemoglobin tetramer ($2\alpha\gamma1_2$) can inhibit the growth of tumor cells. It also gives a better result when combined with the other chemotherapy drug (gemcitabine). A synergistic effect on cancer treatment, inhibiting metastasis and/or reducing recurrence is observed.

INDUSTRIAL APPLICABILITY

The recombinant hemoglobin protein and/or tetramer and/or dimer and/or subunit of the present invention are useful for oxygenation, in targeting cancer cells or tissue or tumor which might be resistant to conventional therapeutic drug for cancer. The chemically modified recombinant hemoglobin protein tetramer and/or dimer and/or subunit of the present invention is also capable of being cleaved or degradable in vivo such that no cytotoxic effect is generated to the subject being administered. The recombinant hemoglobin protein and/or tetramer and/or dimer and/or subunit configured to link with one or more of the conventional therapeutic drug can overcome the resistant problems in some types of cancers or at certain stage of the cancer in patients. The recombinant hemoglobin protein and/or tetramer and/or dimer and/or subunit is readily used for being formulated into pharmaceutical composition and said pharmaceutical composition comprising a therapeutically effective amount of the recombinant hemoglobin protein and/or tetramer and/or dimer and/or subunit with or without linking to one or more therapeutic drug can be used in various applications including oxygenating tissues, treating hemorrhagic shock and oxygen-deprivation disease, and/or targeting drug-resistant cancer cells/tissue.

---

What is claimed is:

1. A recombinant hemoglobin protein, with or without heme, comprising recombinant hemoglobin tetramer as an oxygen carrier and supply replacing natural or native hemoglobin molecule isolated and/or purified from an animal or human source, said recombinant hemoglobin tetramer being $2\alpha\gamma 1_2$ which is non-crosslinked.

2. The recombinant hemoglobin protein of claim 1, wherein said recombinant hemoglobin tetramer is originated from *Homo sapiens*.

3. The recombinant hemoglobin protein of claim 1, wherein each recombinant hemoglobin subunit of said recombinant hemoglobin, tetramer is tagged with a Poly-N or a His tag.

4. A recombinant hemoglobin protein based therapeutic agent for treating cancer comprising the recombinant hemoglobin protein of claim 1 and an active agent, the active agent selected from one or more of a chemotherapeutic agent, a radiotherapeutic agent, a cell labeling agent, and a fluorescent labeling agent, the recombinant hemoglobin protein being either directly conjugated to the active agent or indirectly conjugated to the active agent through a cleavable or non-cleavable linker.

5. The therapeutic agent of claim 4, wherein said recombinant hemoglobin protein is linked with one or more of said linker molecule(s) at one or more subunits of said recombinant hemoglobin protein.

6. The therapeutic agent of claim 4, wherein said recombinant hemoglobin protein is chemically modified by one or more functional groups before being conjugated to said active agent, said chemical modification comprising reacting the recombinant hemoglobin molecule with one or more of the following compound(s) in respect of different chemical reactions for said chemical modification:

a) for amine reactions, the compounds involved comprising anhydride, ketene, NHS ester, isothiocyanates, isocyanates, activated esters comprising fluorophenyl esters and carbonyl azides, sulfonyl chlorides, carbonyls followed by reductive amination, epoxides, carbonates, fluorobenzenes, imidoesters, hydroxymethyl phosphine derivatives, mannich condensation, diazonium derivatives, 4-sulfo-2,3,5,6-tetrafluorophenol, carbonyl diimidazole, sulfo-NHS, and N-terminal modification by pyridoxal-5-phoshpate-based biomimetic transamination;

b) for thiol reactions, the compounds involved comprising maleimides, alkyl halides, haloacetamides, disulfides, thiosulfates, aziridine-containing reagents, acryloyl derivatives, arylating agents, and vinylsulfone derivatives;

c) for carboxylate reactions, the compounds involved comprising diazoalkanes and diazoacetyl compounds, carbonyldiimidazoles, and carbodiimides;

d) for hydroxyl reactions, the compounds involved comprising epoxides and oxiranes, carbonyldiimidazoles, carbonates, chloroformates, chemical and enzymatic oxidations, alkyl halogens, and isocyanates;
e) for native chemical ligations, the compounds involved comprising thioesters;
f) for N-terminal modification, the compounds involved comprising N-terminal serine or threonine using periodate oxidation thereof to generate aldehydes for coupling with hydroxylamines, hydrazines, or hydrazides, carbodiimides;
g) for incorporation of bioorthogonal functionalities, the compounds involved comprising alkynes and azides with subsequent bioorthogonal conjugation reactions comprising dipolar addition Huisgen 1,3-dipolar additions of alkynes and azides, Staudinger ligation of azides and triarylphosphines, Diels-alder reaction of alkenes and tetrazines, and coupling of alkenes and tetrazoles;
h) for photochemical reactions, the compounds involved comprising photoaffinity labeling agents, diazirine derivatives, benzophenones and anthraquinones; and
i) for metal-mediated reactions, the compounds involved comprising metal carbenoids and palladium-activated allyl reagents.

7. The therapeutic agent of claim 4, wherein said cleavable linker comprises carbinolamine, disulfide, carbamide, aminal, carbonate, ester, carbamate, phosphate, amide, acetal, imine, oxime, ether or sulfonamide group linker.

8. The therapeutic agent of claim 4, wherein said chemotherapeutic agent comprises 5-Fluorouracil, temozolomide, cisplatin or other anti-cancer drugs.

9. The therapeutic agent of claim 4, wherein said cancer comprises pancreatic cancer, leukemia, head and neck cancer, colorectal cancer, lung cancer, breast cancer, liver cancer, nasopharyngeal cancer, esophageal cancer, prostate cancer, stomach cancer or brain cancer.

10. A pharmaceutical composition comprising a therapeutically effective amount of the recombinant hemoglobin protein based therapeutic agent of claim 4, said composition being formulated for administration to a subject in need thereof who may suffer from cancer.

11. The composition of claim 10, wherein the therapeutically effective amount of said therapeutic agent is at ≤0.0024 g/kg of said subject and said subject is human.

12. The composition of claim 10, wherein the therapeutically effective amount of said therapeutic agent is at ≤0.03 g/kg of said subject and said subject is animal.

13. The composition of claim 10, wherein route of said administration comprises intravenous injection, intraperitoneal injection, or subcutaneous injection, and said administering of the composition can be in single dose or in multiple doses for once a week.

14. The composition of claim 13, wherein said cancer comprises pancreatic cancer, leukemia, head and neck cancer, colorectal cancer, lung cancer, breast cancer, liver cancer, nasopharyngeal cancer, esophageal cancer or brain cancer.

15. The composition of claim 13, wherein the composition has a pH in a range of 5.5 to 9.5.

16. A method for preparing the therapeutic agent of claim 4, said method comprising:
a) providing a recombinant hemoglobin protein;
b) purifying the recombinant hemoglobin protein using different column chromatography methods; and
c) chemically modifying the recombinant hemoglobin protein comprising reacting with one or more functional groups followed by conjugating said recombinant hemoglobin protein with an active agent, or conjugating an active agent with a cleavable or non-cleavable linker to form a linker-active agent conjugate prior to linking said conjugate to said recombinant hemoglobin protein.

17. The method of claim 16, wherein said chemically modifying comprises one or more of the following reactions or modifications:
a) amine reactions, wherein the compounds involved comprises anhydride, ketene, NHS ester, isothiocyanates, isocyanates, activated esters comprising fluorophenyl esters and carbonyl azides, sulfonyl chlorides, carbonyls followed by reductive amination, epoxides, carbonates, fluorobenzenes, imidoesters, hydroxymethyl phosphine derivatives, mannich condensation, diazonium derivatives, 4-sulfo-2,3,5,6-tetrafluorophenol, carbonyl diimidazole, sulfo-NHS, and N-terminal modification by pyridoxal-5-phoshpate-based biomimetic transamination;
b) thiol reactions, wherein the compounds involved comprises maleimides, alkyl halides, haloacetamides, disulfides, thiosulfates, aziridine-containing reagents, acryloyl derivatives, arylating agents, and vinylsulfone derivatives;
c) carboxylate reactions, wherein the compounds involved comprises diazoalkanes and diazoacetyl compounds, carbonyldiimidazoles, and carbodiimides;
d) hydroxyl reactions, wherein the compounds involved comprises epoxides and oxiranes, carbonyldiimidazoles, carbonates, chloroformates, chemical and enzymatic oxidations, alkyl halogens, and isocyanates;
e) native chemical ligations, wherein the compounds involved comprises thioesters;
f) N-terminal modification, wherein the compounds involved comprises N-terminal serine or threonine using periodate oxidation thereof to generate aldehydes for coupling with hydroxylamines, hydrazines, or hydrazides, carbodiimides;
g) incorporation of bioorthogonal functionalities, wherein the compounds involved comprises alkynes and azides with subsequent bioorthogonal conjugation reactions comprising dipolar addition Huisgen 1,3-dipolar additions of alkynes and azides, Staudinger ligation of azides and triarylphosphines, Diels-alder reaction of alkenes and tetrazines, and coupling of alkenes and tetrazoles;
h) photochemical reactions, wherein the compounds involved comprises photoaffinity labeling agents, diazirine derivatives, benzophenones and anthraquinones; and
i) metal-mediated reactions, wherein the compounds involved comprises metal carbenoids and palladium-activated allyl reagents.

18. The method of claim 16, wherein said cleavable linker comprises carbinolamine, disulfide, carbamide, aminal, carbonate, ester, carbamate, phosphate, amide, acetal, imine, oxime, ether or sulfonamide group linker.

19. The method of claim 16, wherein said active agent is a chemotherapeutic agent comprising 5-Fluorouracil, temozolomide, cisplatin or other anti-cancer drug.

20. A method for locally oxygenating tissue from or in an animal or human subject comprising applying a pharmaceutical composition comprising the recombinant hemoglobin protein of claim 1.

21. The method of claim 20, wherein the tissue is hypoxic.

22. A method for treating oxygen-deprivation disorder in an animal or human subject comprising administering a pharmaceutical composition comprising the recombinant hemoglobin protein of claim 1 to said animal or human subject in need thereof.

23. A method for treating hemorrhagic shock in an animal or human subject comprising administering a pharmaceutical composition comprising the recombinant hemoglobin protein of claim 1 to said animal or human subject in need thereof.

24. A method for targeting and inducing apoptosis of cancer cells comprising administering the composition of claim 10 to a subject in need thereof.

25. A method for inhibiting tumor metastasis and reducing recurrence comprising administering the composition of claim 10.

\* \* \* \* \*